United States Patent
Klumpers et al.

(10) Patent No.: US 10,702,495 B2
(45) Date of Patent: Jul. 7, 2020

(54) METHOD AND COMPOSITIONS FOR TREATING DYSTROPHIES AND MYOTONIA

(71) Applicant: Nexien Biopharma, Inc., Glendale, CO (US)

(72) Inventors: Linda Klumpers, Denver, CO (US); Benedikt Schoser, Munich (DE); Robert Goldfarb, Hollywood, FL (US); Jeffrey Friedland, Denver, CO (US)

(73) Assignee: Nexien Biopharma, Inc., Glendale, CO (US)

( * ) Notice: Subject to any disclaimer, the term of this patent is extended or adjusted under 35 U.S.C. 154(b) by 0 days.

(21) Appl. No.: 16/435,756

(22) Filed: Jun. 10, 2019

(65) Prior Publication Data

US 2019/0358197 A1 Nov. 28, 2019

Related U.S. Application Data

(63) Continuation-in-part of application No. 15/899,160, filed on Feb. 19, 2018, now abandoned.

(60) Provisional application No. 62/460,941, filed on Feb. 20, 2017.

(51) Int. Cl.
| | |
|---|---|
| *A61K 31/352* | (2006.01) |
| *A61K 31/05* | (2006.01) |
| *A61K 9/00* | (2006.01) |
| *A61P 21/00* | (2006.01) |
| *A61K 47/44* | (2017.01) |
| *A61K 31/353* | (2006.01) |

(52) U.S. Cl.
CPC ............ *A61K 31/352* (2013.01); *A61K 9/006* (2013.01); *A61K 31/05* (2013.01); *A61K 47/44* (2013.01); *A61P 21/00* (2018.01)

(58) Field of Classification Search
CPC .............................. A61K 31/352; A61P 21/00
See application file for complete search history.

(56) References Cited

U.S. PATENT DOCUMENTS

| | | | |
|---|---|---|---|
| 2,798,053 A | 7/1957 | Brown | |
| 2,909,462 A | 10/1959 | Warfield et al. | |
| 3,560,528 A | 2/1971 | Petrzilka | |
| 3,668,224 A | 6/1972 | Petrzilka | |
| 4,025,516 A | 5/1977 | Razdan et al. | |
| 4,207,893 A | 6/1980 | Michaels | |
| 4,327,725 A | 5/1982 | Cortese | |
| 4,855,294 A | 8/1989 | Patel et al. | |
| 4,915,949 A | 4/1990 | Wong et al. | |
| 5,349,945 A | 9/1994 | Wass et al. | |
| 5,394,868 A | 3/1995 | Ambrosio et al. | |
| 5,429,816 A | 7/1995 | Hofrichter et al. | |
| 5,552,136 A | 9/1996 | Motley | |
| 5,643,588 A | 7/1997 | Roe et al. | |
| 5,674,472 A | 10/1997 | Akehurst et al. | |
| 5,766,573 A | 6/1998 | Purewal et al. | |
| 5,860,419 A | 1/1999 | Davies et al. | |
| 6,419,954 B1 | 7/2002 | Chu et al. | |
| 6,521,212 B1 | 2/2003 | Cloutier et al. | |
| 6,641,800 B1 | 11/2003 | Mistry et al. | |
| 6,703,418 B2 | 3/2004 | Plasse | |
| 6,946,120 B2 | 9/2005 | Wai-Chiu So et al. | |
| 7,186,850 B2 | 3/2007 | Silverberg et al. | |
| 7,344,736 B2 | 3/2008 | Whittle et al. | |
| 7,449,613 B2 | 11/2008 | Klofta et al. | |
| 7,524,881 B2 | 4/2009 | Goodwin et al. | |
| 7,674,922 B2 | 3/2010 | Burdick et al. | |
| 8,222,292 B2 | 7/2012 | Goskonda et al. | |
| 8,324,408 B2 | 12/2012 | Erler et al. | |
| 8,530,670 B2 | 9/2013 | Heiser et al. | |
| 8,741,341 B2 | 6/2014 | Goskonda et al. | |
| 8,895,078 B2 | 11/2014 | Mueller | |
| 9,034,395 B2 | 5/2015 | Whittle | |
| 9,339,507 B2 | 5/2016 | Olschewski | |
| 9,345,771 B2 | 5/2016 | Goskonda | |
| 2004/0265238 A1 | 12/2004 | Chaudry | |
| 2007/0269379 A1 | 11/2007 | Mitragotri et al. | |

OTHER PUBLICATIONS

Montagnese et al. Journal of Neurology, 2019, vol. 266, pp. 530-532 (Year: 2019).*
Montagnese et al. Journal of Neurology, 2020, vol. 267, pp. 415-421 (Year: 2020).*
Berard et al., "A Motor Function Measure Scale for Neuromuscular Diseases. Construction and Validation Study," Neuromuscular Disorders 15 (2005) pp. 463-470.
Bergamaschi et al., "Cannabidiol Reduces the Anxiety Induced by Simulated Public Speaking in Treatment-Naïve Social Phobia Patients," Neuropsychoparhamcology (2011) 36: 1219-1226.
Cilio et al., "Cannabidiol: Pharmacology and potential therapeutic role in epilepsy and other neuropsychiatric disorders," Epilepsia (2014) 55(6): 791-802.
Dalton et al., "Influence on cannabidiol on delta-9-tetrahydrocannabinol effects," Clinical Pharmacology and Therapeutics, 19(3): 300-309.
De Souza Crippa et al., "Effects of Cannabidiol (CBD) on Regional Cerebral Blood Flow," Neuropsychoparhamcology (2004) 29: 417-426.
Devinsky et al., "Trial of Cannabidiol for Drug-Resistant Seizures in the Dravet Syndrome," The New England Journal of Medicine (2017) 376 (21): 2011-2020.
Foff et al., "Therapeutic Development in Myotonic Dystrophy Type I," Muscle Nerve, 2011 44(2) 160-169.
Fusar-Poli et al., "Distinct Effects of Δ9-Tetrahydrocannabinol and Cannabidiol on Neural Activation During Emotional Processing," Arch Gen Psychiatry (2009), 66(1): 95-105.
Gomes-Pereira et al., "Myotonic dystrophy mouse models: towards rational therapy development," Trends in Molecular Medicine (2011):1-12.
Gronemeier et al., "Nonsense and Missense Mutations in the Muscular Chloride Channel Gene Clc-1 of Mytonic Mice," The Journal of Biological Chemistry (1994), 269(8): 5963-5967.

(Continued)

*Primary Examiner* — James D. Anderson
(74) *Attorney, Agent, or Firm* — Joseph F. Aceto, Esq.

(57) ABSTRACT

Methods and compositions for treating myotonia and dystrophies.

17 Claims, No Drawings

(56) References Cited

OTHER PUBLICATIONS

Guy et al., "A Phase I, Double Blind, Three-Way Crossover Study to Assess the Pharmacokinetic Profile of Cannabis Based Medicine Extract (CBME) Administered Sublingually in Variant Cannabinoid Ratios in Normal Healthy Male Volunteers (GWPK0215)," Cannabis: From Pariah to Prescription (ed: Ethan Russo) The Haworth Integrative Healing Press (2003), pp. 121-152.

Haney et al., "Oral Cannabidiol does not Alter the Subjective, Reinforcing or Cardiovascular Effects of Smoked Cannabis," Neuropsychopharmacology (2016), 41: 1974-1982.

Heatwole et al., "The Myotonic Dystrophy Health Index: Correlations with Clinical Tests and Patient Function," Muscle Nerve, (2016) 53(2) 183-190.

Hindocha et al., "Acute effects of delta-9-tetrahydrocannabinol, cannabidiol and their combination on facial emotion recognition: A randomised, double-blind, placebo-controlled study in cannabis users," European Neuropsychopharamcology (2015), 25:325-334.

Jahromi, "Advances in Myotonic Dystrophy Type 1 Drug Discovery Through Design of Novel Ligands and Mechanism Establishment," University of Illinois at Urbana-Champaign, 2013.

Johnson et al., "Multicenter, Double-Blind, Randomized, Placebo-Controlled, Parallel-Group Study of the Efficacy, Safety, and Tolerability of THC:CBD Extract and THC Extract in Patients with Intractable Cancer-Related Pain," Journal of Pain and Symptom Management (2010), 39(2): 167-179.

Karniol, et al., "Cannabidiol Interferes with the Effects of delta-9-tetrahydrocannabinol in Man," European Journal of Pharmacology (1974) 28: 172-177.

Leweke et al., "Different Effects of Nabilone and Cannabidiol on Binocular Depth Inversion in Man," Pharmacol Biochem Behav (1999), 66(1): 175-181.

Logigian et al., "Leukocyte CTG repeat length correlates with severity of myotonia in myotonic dystrophy type 1," Neurology (2004), 62(7) 1-25.

Logigian et al., "Mexiletine is an Effective Antimyotonia Treatment in Myotonic Dystrophy Type 1," Neurology, (2010) 74(18), pp. 1441-1448.

Morgan et al., "Impact of cannabidiol on the acute memory and psychotomimetic effects of smoked cannabis: naturalistic study," The British Journal of Psychiatry (2010), 197: 285-290.

Nadulski et al., "Randomized, Double-Blind, Placebo-Controlled Study About the Effects of Cannabidiol (CBD) on the Pharmacokinetics of delta-9-Tetrahydrocannabinol (THC) After Oral Application of THC Verses Standardized Cannabis Extract," Ther Drug Monit (2005), 27(6): 799-810.

Nicholson et al., "Effect of delta-9-Tetrahydrocannabinol and Cannabidiol on Noctournal Sleep and Early-Morning Behavior in Young Adults," J Clin Psychopharmacol (2004), 24: 305-313.

Sativex Oromucosal Spray [summary of product characteristics]. Cambridge, UK: GW Pharma, Ltd.: 2015.

Sativex® Oromucosal Spray [package insert]. Reading, UK: Bayer, plc; 2017.

Sativex® Oromucosal Spray [prescribing information]. Reading, UK: Bayer, plc.: 2017.

Staunton et al., "Identification of secondary effects of hyperexcitability by proteomic profiling of myotonic mouse muscle," Mol. BioSyst. (2011), 7: 2480-2489.

Wade et al., "Do cannabis-based medicinal extracts have general or specific effects on symptoms in multiple sclerois? A double-blind, randomized, placebo-controlled study on 160 patients," Mult Schler (2004) 10: 434-441.

Zuardi et al., "Action of Cannabidiol on the Anxiety and Other Effects Produced by delta-9-THC in Normal Subjects," Psychopharmacology (1982) 76: 245-250.

Zuardi et al., "Effects of ipsapirone and cannabidiol on human experimental anxiety," Journal of Psychopharmacology (1993), 7(1):82-88.

Zuardi et al., "Inverted U-Shaped Dose-Response Curve of the Anxiolytic Effect of Cannabidiol during Public Speaking in Real Life," Frontiers in Pharmacology (2017), 8(259): 1-9.

Karschner et al. (2011), "Subjective and Physiological Effects after Controlled Sativex and Oral THC Administration," Clin Pharmcol Ther. 89(3): 1-15.

Karschner et al. (2011), "Plasma Cannabinoid Pharmacokinetics Following Controlled Oral Δ9-Tetrahydrocannabinol and Oromucosal Cannabis Extract Administration," Clinical Chemistry 57(1): 66-75.

Guy et al. (2003), "A Phase I, Open Label, Four-Way Crossover Study to Compare the Pharmacokinetic Profiles of a Single Dose of 20 mg of a Cannabis Based Medicine Extract (CBME) Administered on 3 Different Areas of the Buccal Mucosa and to Investigate the Pharmacokinetics of CBME per Oral in Healthy Male and Female Volunteers (GWPK0112)," Cannabis: From Pariah to Prescription (ed: Ethan Russo) The Haworth Integrative Healing Press (2003), pp. 79-118.

Suominen et al., "P2.32: The frequency of myotonic dystrophy type 2 (DM2) and type 1 (DM1) mutations in the population," Abstracts / Neuromuscular Disorders (2010), 20(9-10): 628.

Suominen et al., "Population frequency of myotonic dystrophy: higher than expected frequency of myotonic dystrophy type 2 (DM2) mutation in Finland," European Journal of Human Genetics (2011) 19: 776-782.

* cited by examiner

METHOD AND COMPOSITIONS FOR TREATING DYSTROPHIES AND MYOTONIA

CROSS REFERENCE TO RELATED APPLICATIONS

This application is a continuation-in-part application of U.S. application Ser. No. 15/899,160, filed on Feb. 19, 2018, which is a non-provisional application, which claims the benefits of U.S. Provisional Patent Application Ser. No. 62/460,941 filed on Feb. 20, 2017 and are incorporated herein by reference.

TECHNICAL FIELD OF THE INVENTION

The present invention relates to methods and compositions for treating myotonia and dystrophies such as muscular dystrophies. The methods comprise the administration of a composition comprising a cannabinoid and/or a terpene to a patient in need of such treatment.

BACKGROUND OF THE INVENTION

Myotonia is a condition present in a number of neuromuscular disorders such as myotonia congenital, paramyotonia congenital and myotonic dystrophy, and is characterized by a delayed relaxation of muscles after voluntary contraction.

Muscular dystrophy is a general term that describes a group of genetic muscular diseases wherein muscles weaken and breakdown over time without involvement of the nervous system. Some of the more common types of muscular dystrophy include:

Duchenne Muscular Dystrophy which is the most common muscular dystrophy that begins in early childhood and is characterized by increasing weakness in the pelvic and shoulder girdles that eventually leads to respiratory and heart failures;

Becker Muscular Dystrophy which is a less severe form of Duchenne Muscular Dystrophy which has a later patient onset and slower progression than Duchenne Muscular Dystrophy;

Emery-Dreifus Muscular Dystrophy which begins early in a patient's life and is characterized by a slowly progressive weakening of the upper arm and pelvic girdle, but the muscles are not hypertrophied;

Facioscapulohumeral Muscular Dystrophy which is a relative benign form wherein the muscles of the face, shoulder girdle, and arm atrophy;

Limb-Girdle Muscular Dystrophy which is a slowly progressive form that may affect either males or females, and is characterized by a weakening or wasting of the pelvic girdle or shoulder girdle;

Myotonic Muscular Dystrophy which is a rare slowly progressive disorder characterized by myotonia followed by atrophy of the muscles including the muscles of the face and neck, cataracts, hypogonadism, frontal balding and cardiac abnormalities; and Oculopharyngeal Muscular Dystrophy which has an adult onset and is characterized by a weakness of the external ocular and pharyngeal muscles that causes ptosis, ophthalmoplegia and dysphagia.

There are currently no known cures for muscular dystrophy, however, various drugs have been administered to manage the various symptoms. For example, Foff et al., "Therapeutic Development in Myotonic Dystrophy Type I," Muscle Nerve, 2011 44(2) 160-169, indicates that drugs such as mexelitine, dehydroepiandrosterone (DHEA) and exogenous insulin-like growth factor (IGF1) have been tried as treatment options without great success. The doctoral dissertation of Amin Haghighat Jahromi, entitled "Advances in Myotonic Dystrophy Type 1 Drug Discovery Through Design of Novel Ligands and Mechanism Establishment," University of Illinois at Urbana-Champaign 2013, suggests kanamycin, pentamidine, neomycin B, melamine-acridine conjugate N,N'-(propane-1,3-diylbis(azanediyl))bis(propane-3,1-diyl))bis(9-((4-((4,6-diamino-1,3,5-triazin-2-yl)amino)butyl)amino)acridine-4-carboxamide and Hoechst 33528 which has the following structure:

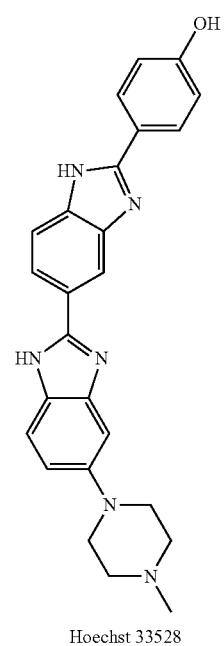 [SMILES: CN1CCN(c2ccc3[nH]c(-c4ccc5[nH]c(-c6ccc(O)cc6)nc5c4)nc3c2)CC1]

Hoechst 33528 may be useful in treating myotonic dystrophy. The Jahromi dissertation also states that palliative therapy for myotonic dystrophy includes the administration of known compounds such as selenium, vitamin E, baclofen, nifedipine, creatine monohydrate, testosterone, DHEA and bioflavonoids.

It is an object of the present invention to provide methods and compositions that are effective in treating dystrophies such as Duchenne Muscular Dystrophy, Becker Muscular Dystrophy, Emery-Dreifus Muscular Dystrophy, Facioscapulohumeral Muscular Dystrophy, Limb-Girdle Muscular Dystrophy, Myotonic Muscular Dystrophy, or Oculopharyngeal Muscular Dystrophy.

It is a further object of the present invention to provide methods and compositions that are effective in treating myotonia, including myotonia associated with myotonia congenital, paramytonia congenital and myotonic dystrophy.

It is an additional object of the present invention to provide methods and compositions that are effective in treating myotonic dystrophy, including myotonic dystrophy type 1 (DM1) and myotonic dystrophy type 2 (DM2).

SUMMARY OF THE INVENTION

The present invention accomplishes the above objectives and others by providing a method of treating dystrophies and/or myotonia comprising the administration of a composition comprising at least one cannabinoid, at least one terpene, or a combination of at least one cannabinoid and at least one terpene.

The administration may be topical, oral, nasal, inhalation or a combination thereof.

If the composition is administered topically, it may be applied to a patient's skin in the form of a patch, gel, cream, paste, lotion, ointment, salve, serum, spray, aerosol, mousse or foam.

If the composition is administered orally, it may be provided in a solid or liquid form that may be swallowed or held in the oral cavity. The solid oral form may be a tablet, capsule, powder, or sachet, and may be administered in the solid form or dispersed or mixed with a food such as applesauce or oatmeal, or water, for easier swallowing. The liquid oral form may be a solution, suspension or syrup that may be swallowed or applied to the oral cavity as a spray, mist, aerosol or drops.

If the composition is administered nasally, it may be in form of a spray, mist or powder that is applied to the nasal cavity.

If the composition is administered via inhalation, the composition may be delivered to a patient's respiratory system via a nebulizer, vaporization or a metered dose inhaler.

The at least one cannabinoid may be synthetic or naturally occurring, and is preferably selected from the group consisting of tetrahydrocannabinol (THC), cannabidiol (CBD), cannabinol (CBN), cannabigerol (CBG), cannabichromene (CBC), tetrahydrocannabidivarin (THCV), tetrahydrocannabinolic acid (THCA), cannabidivarin (CBDV), cannadidiolic acid (CBDA), the various isomers and enantiomers thereof, and combinations and mixtures of one or more of the forgoing.

The at least one terpene may be synthetic or naturally occurring, and is preferably selected from the group consisting of limonene, pinene, linalool, caryophyllene, caryophyllene oxide, nerolidol, phytol, myrcene, 1-8-cineole (aka eucalyptol), pulegone, teroineol, terpinolene, the various isomers and enantiomers thereof, and combinations and mixtures of one or more of the forgoing.

DETAILED DESCRIPTION OF THE INVENTION

Except where noted, all terms are intended to have their normal meaning in the art, and are used as they would have been used by a person of ordinary skill at the time of the disclosure. It should be understood that throughout this application the singular forms, such as "a," "an," and "the," are often used for convenience, however, these singular forms are intended to encompass the plural unless otherwise specified, or unless the context clearly calls for the singular alone. It should also be understood that all publication, patents, books, journal articles, and the like, which are referred to in this application, are incorporated by reference in their entirety and for all purposes to the extent not inconsistent with the present disclosure.

As used herein the term "myotonia" refers to any disorder or condition characterized by tonic spasm or temporary rigidity of a muscle and in particular the decreased relaxation of a muscle following a sustained contraction. Examples of disorders that exhibit myotonia include myotonic dystrophy, myotonia congenital, and paramyotonia congenital.

As used herein, the term "dystrophy" refers to any disorder or condition, particularly genetic conditions, characterized by degeneration in tissues, such as muscular tissue. Examples of muscular dystrophies include Duchenne Muscular Dystrophy, Becker Muscular Dystrophy, Emery-Dreifus Muscular Dystrophy, Facioscapulohumeral Muscular Dystrophy, Limb-Girdle Muscular Dystrophy, Myotonic Muscular Dystrophy, and Oculopharyngeal Muscular Dystrophy.

As used herein, the terms "treat," "treating" or "treatment" refers to providing relief of one or more of the symptoms associated with a particular condition or diminishing or lessening any one or more of the symptoms associated with the condition.

As used herein, "transdermal" means delivery of a drug or biologically active substance by passage into and through the skin or mucosal tissue. Hence, the terms "transdermal" and "transmucosal" are used interchangeably unless specifically stated otherwise. Likewise, the terms "skin," "derma," "epidermis," "mucosa" and the like will also be used interchangeably unless specifically stated otherwise.

As used herein, the term "topical" refers to outer skin or derma of a patient. Hence, the phrase "topical application" refers to the application of a composition of the present invention and its various embodiments to the outer surface of a patient's skin or derma.

As used herein, the terms "occlude," "occluded," "occlusive" and the like refer to a transdermal formulation that is applied to the skin with the use of a supporting or otherwise associated structure. In other words, a topical formulation may be applied to the skin of a patient with the aid of a structure, such as a backing member, bandage or cover. A matrix patch is an example of an occluded device. Conversely, "unoccluded" and "non-occluded," which may be used interchangeably, refer to a transdermal formulation that is applied to the skin without the use of a support, backing member, cover or otherwise associated structure. In other words, the transdermal formulation is applied to the skin in a free form, which is sufficient to effect transdermal delivery of the drug or biologically active substance without the use of structures, such as a backing member, etc. A gel formulation is an example of a non-occluded composition; other non-occluded compositions include ointments, lotions, pastes, mousses, aerosols and creams.

Concentration, weight percent and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a percent range of 1% to 20% should be interpreted to include not only the explicitly recited percent limits of 1% and 20% but also to include individual percentages such as 1.25%, 2.49%, 3%, 4.75%, 8.34% and sub-ranges such as 1% to 5%, 10% to 15%, 4.7% to 11.9% etc.

As used herein the term "cannabinoid" refers to any chemical known to activate cannabinoid receptors in cells. The cannabinoids may be synthetic or naturally occurring. Naturally occurring cannabinoids may be found in *Cannabis* plants or produced endogenously in humans and other animals. If produced endogenously, the cannabinoids are sometimes referred to as endocannabinoids. Synthetic cannabinoids are chemicals with similar structures to plant cannabinoids or endocannabinoids. Naturally occurring cannabinoids may be extracted and purified from various plants such as the *Cannabis* plant, using known methods such as those described in U.S. Pat. Nos. 7,344,736; 8,895,078 and 9,034,395 which are incorporated herein by reference. Synthetic cannabinoids are commercially available and can be prepared by known methods such as those described in U.S. Pat. Nos. 3,668,224; 3,560,528; 7,186,850; 7,524,881; 7,674,922; 8,324,408 and 8,530,670, which are incorporated herein by reference.

Examples of cannabinoids that may be used in the methods of treatment and compositions in accordance with the present invention include:

Cannabigerolic Acid (CBGA);
Cannabigerolic Acid monomethylether (CBGAM);
Cannabigerol (CBG);
Cannabigerol monomethylether (CBGM);
Cannabigerovarinic Acid (CBGVA);
Cannabigerovarin (CBGV);
Cannabichromenic Acid (CBCA);
Cannabichromene (CBC);
Cannabichromevarinic Acid (CBCVA);
Cannabichromevarin (CBCV);
Cannabidiolic Acid (CBDA);
Cannabidiol (CBD);
Cannabidiol monomethylether (CBDM);
Cannabidiol-$C_4$ (CBD-$C_4$);
Cannabidivarinic Acid (CBDVA);
Cannabidivarin (CBDV);
Cannabidiorcol (CBD-$C_1$);
Tetrahydrocannabinolic acid A (THCA-A);
Tetrahydrocannabinolic acid B (THCA-B);
Tetrahydrocannabinol (THC);
Tetrahydrocannabinolic acid $C_4$ (THCA-$C_4$);
Tetrahydrocannbinol $C_4$ (THC-$C_4$);
Tetrahydrocannabivarinic acid (THCVA);
Tetrahydrocannabivarin (THCV);
Tetrahydrocannabiorcolic acid (THCA-$C_1$);
Tetrahydrocannabiorcol (THC-$C_1$);
$\Delta^7$-cis-iso-tetrahydrocannabivarin ($\Delta^7$-THCV);
$\Delta^8$-tetrahydrocannabinolic acid ($\Delta^8$-THCA);
$\Delta^8$-tetrahydrocannabinol ($\Delta^8$-THC);
Cannabicyclolic acid (CBLA);
Cannabicyclol (CBL);
Cannabicyclovarin (CBLV);
Cannabielsoic acid A (CBEA-A);
Cannabielsoic acid B (CBEA-B);
Cannabielsoin (CBE);
Cannabinolic acid (CBNA);
Cannabinol (CBN);
Cannabinol methylether (CBNM);
Cannabinol-$C_4$ (CBN-$C_4$);
Cannabivarin (CBV);
Cannabino-$C_2$ (CBN-$C_2$);
Cannabiorcol (CBN-$C_1$);
Cannabinodiol (CBND);
Cannabinodivarin (CBDV);
Cannabitriol (CBT);
10-Ethoxy-9-hydroxy-$\Delta^{6a}$-tetrahydrocannabinol;
8,9-Dihydroxy-$\Delta^{6a(10a)}$-tetrahydrocannabinol (8,9-Di-OH-CBT-$C_5$);
Cannabitriolvarin (CBTV);
Ethoxy-cannabitriolvarin (CBTVE);
Dehydrocannabifuran (DCBF);
Cannbifuran (CBF);
Cannabichromanon (CBCN);
Cannabicitran (CBT);
10-Oxo-$\Delta^{6a(10a)}$-tetrahydrocannabinol (OTHC);
$\Delta^9$-cis-tetrahydrocannabinol (cis-THC);
Cannabiripsol (CBR);

3,4,5,6-tetrahydro-7-hydroxy-alpha-alpha-2-trimethyl-9-n-propyl-2,6-metha-no-2H-1-benzoxocin-5-methanol (OH-iso-HHCV); and Trihydroxy-$\Delta^9$-tetrahydrocannabinol (triOH-THC).

Preferably the cannabinoid may be selected from the group consisting of: Tetrahydrocannabinol (THC) having the following structural formula:

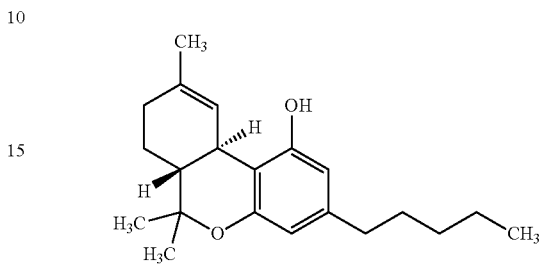

Cannabidiol (CBD) having the following structural formula:

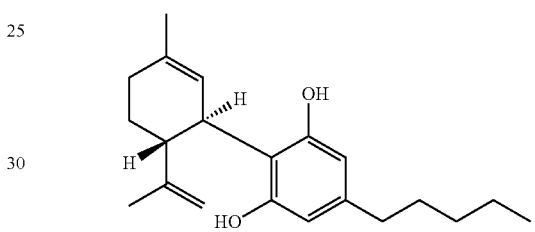

Cannabinol (CBN) having the following structural formula:

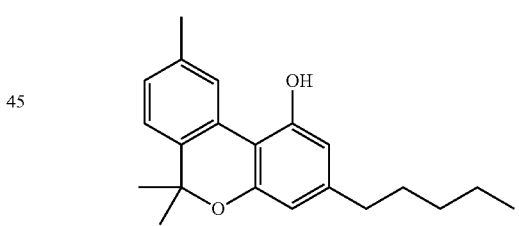

Cannabigerol (CBG) having the following structural formula:

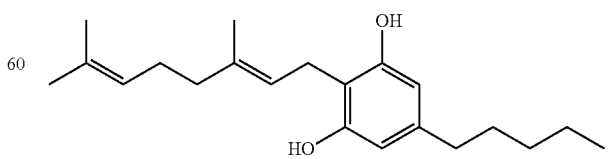

Cannabichromene (CBC) having the following structural formula:

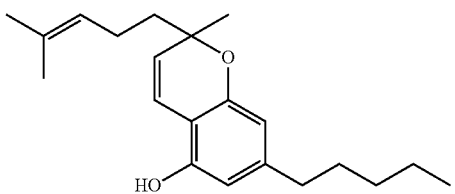 [SMILES: CCCCCc1cc(O)c2c(c1)OC(C)(CCC=C(C)C)C=C2]

Tetrahydrocannabidivarin (THCV) having the following structural formula:

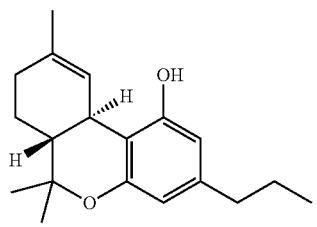 [SMILES: CCCc1cc(O)c2c(c1)OC(C)(C)[C@@H]1CCC(C)=C[C@@H]21]

Tetrahydrocannabinolic acid (THCA) having the following structural formula:

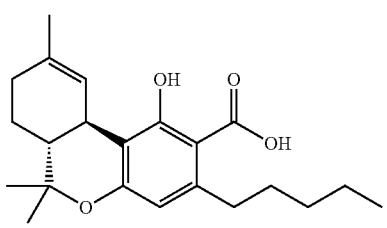 [SMILES: CCCCCc1cc2c(c(O)c1C(=O)O)[C@@H]1C=C(C)CC[C@H]1C(C)(C)O2]

Cannabidivarin (CBDV) having the following structural formula:

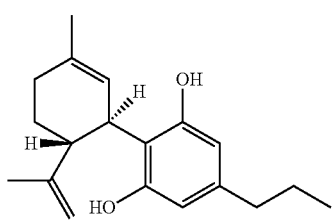 [SMILES: C=C(C)[C@@H]1CCC(C)=C[C@H]1c1c(O)cc(CCC)cc1O]

Cannadidiolic acid (CBDA) having the following structural formula:

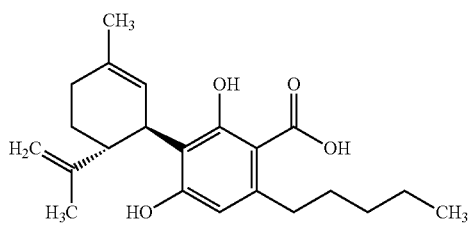

Cannabielsoin (CBE) having the following structural formula:

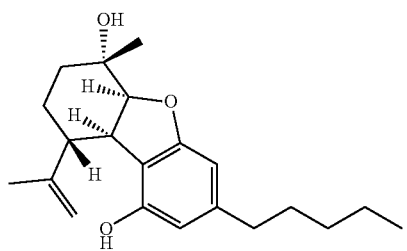

Cannabicyclol (CBL) having the following structural formula:

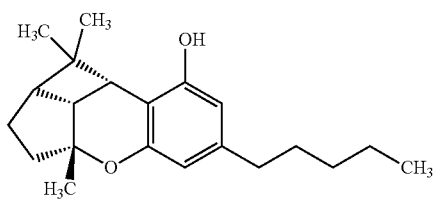

Cannabinodiol (CBND) having the following structural formula:

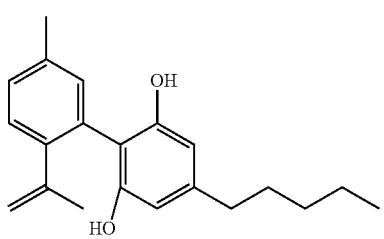 [SMILES: C=C(C)c1ccc(C)cc1-c1c(O)cc(CCCCC)cc1O]

and a mixture of the forgoing.

The most preferred cannabinoid is selected from the group consisting of tetrahydrocannabinol (THC), cannabidiol (CBD), cannabinol (CBN), cannabigerol (CBG), cannabichromene (CBC), tetrahydrocannabidivarin (THCV), tetrahydrocannabinolic acid (THCA), cannabidivarin (CBDV), cannadidiolic acid (CBDA), the various isomers and enantiomers thereof, and combinations and mixtures of one or more of the forgoing. The above-identified cannabinoids may also be present as pharmaceutically acceptable salts or as individual isomers, enantiomers or mixtures thereof.

As used herein, the term "terpene" means an organic compound containing an isoprene unit, i.e., $(C_5H_8)_n$ of the general formula:

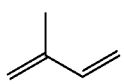

wherein n is a whole integer of 1 or greater.

Unless otherwise stated, the term "terpene" includes terpenoids which are known in the art to be a compound wherein the base isoprene unit, $(C_5H_8)_n$, has been modified to include a functional group.

The term terpene includes:

Hemiterpenes which consist of a single isoprene unit, i.e., n=1, representative examples include isoprene, prenol and isovaleric acid;

Monoterpenenes which consist of two isoprene units, i.e., n=2, representative examples include geraniol, terpineol, limonene, myrcene, linalool and pinene;

Sesquiterpenes which consist of three isoprene units, i.e., n=3, representative examples include humulene, farnesenes and farnesol;

Diterpenes which consist of four isoprene units, i.e., n=4, representative examples include cafestol, kahweol, cembrene, and taxadiene;

Sesterterpenes which consist of five isoprene units, i.e., n=5, representative example includes geranylfarnesol;

Triterpenes which consist of six isoprene units, i.e., n=6, representative example includes squalene;

Sesquarterpenes which include seven isoprene units, i.e., n=7, representative examples include ferrugicadiol and tetraprenylcurcumene;

Tetraterpenes which contain eight isoprene units, i.e., n=8 representative examples include acyclic lycopene, moncyclic gamma-carotene, bicyclic alpha carotene and bicyclic beta carotene; and Polyterpenes which consist of long isoprene chains, i.e., n>8.

The term terpenes as used herein also includes terpene esters, terpenoids, terpenoid oxides, or their derivatives such as pharmaceutically acceptable salts and specific isomeric forms.

Representative examples of terpenes include:

Bisabolol, a monocyclic sesquiterpene alcohol and can be present in a racemic mixture, purified α or β forms or various ratios of the α or β forms. The α form has the following structural formula:

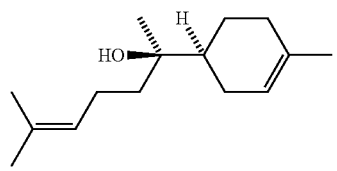 [SMILES: CC(C)=CCC[C@@](C)(O)[C@@H]1CC=C(C)CC1]

The β form has the following structural formula:

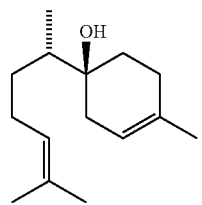 [SMILES: CC(C)=CCC[C@H](C)[C@@]1(O)CC=C(C)CC1]

Cadinene, an isomeric hydrocarbon sesquiterpene and can be present in a racemic mixture, purified α or γ forms or various ratios of the α or γ forms. The α form has the following structural formula:

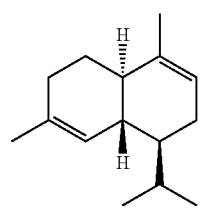

The γ form has the following structural formula:

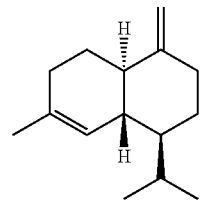

Cafestol, a diterpene molecule having the following structural formula:

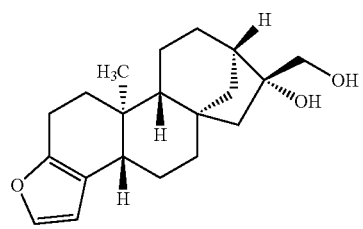

Camphene, a bicyclic monoterpene having the following structural formula:

Camphor, a terpenoid having the following structural formula:

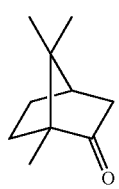

Carene, a bicyclic monoterpene having the following structural formula:

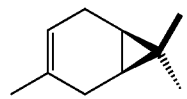

Carotene, having the following structural formula:

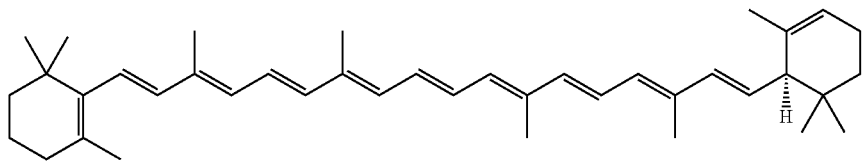 [SMILES: CC1=CCCC(C)(C)[C@H]1/C=C/C(C)=C/C=C/C(C)=C/C=C/C=C(C)/C=C/C=C(C)/C=C/C1=C(C)CCCC1(C)C]

As used herein, the term carotene refers to any of the isomeric forms of carotene and/or mixture thereof in any ratio.

Carvacrol, a monoterpenoid phenol having the following structural formula:

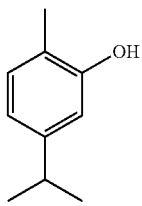

Carvone, a monoterpenoid that can be also present in a racemic mixture, purified enantiomer forms S-(+) and R-(−) or various ratios of the enantiomer forms S-(+) and R-(−). The S-(+) enantiomer of carvone has the following structural formula:

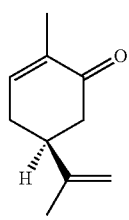

The R-(−) enantiomer of carvone has the following structural formula:

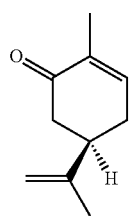

Caryophyllene (a.k.a. β-Caryophyllene), a bicyclic sesquiterpene having the following structural formula:

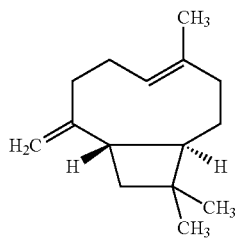

Caryophyllene oxide, having the following structural formula:

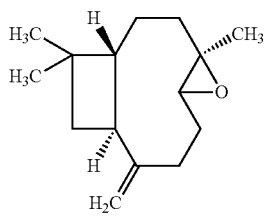

Cedrene, which can be present in a racemic mixture, purified α or β forms, or various ratios of the α or β forms. The α form has the following structural formula:

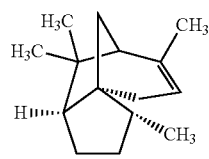

The β form has the following structural formula:

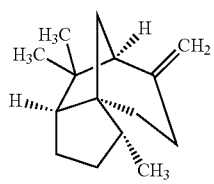

Cedrol, a sesquiterpene alcohol having the following structural formula:

Cembrene, a monocyclic diterpene having the following structural formula:

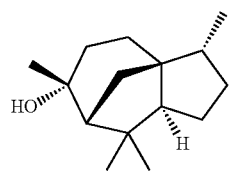 [SMILES: C[C@@H]1CC[C@H]2C(C)(C)[C@H]3C[C@@]12CC[C@@]3(C)O]

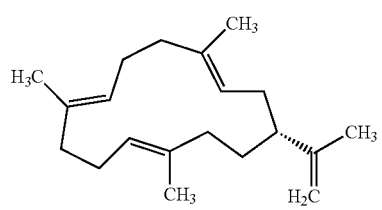 [SMILES: C=C(C)[C@H]1C/C=C(\C)CC/C=C(\C)CC/C=C(\C)CC1]

Citronellal, a monoterpenoid having the following structural formula:

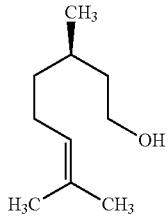

Citronellol, an acyclic monoterpenoid which includes either or both of the (+) and (−) enantiomers as pure forms or mixtures in any ratio. The (+) enantiomer has the following structural formula:

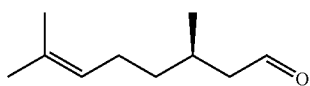

The (−) form has the following structural formula:

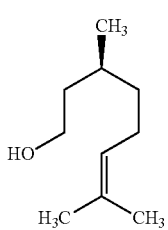

Dehydrovomifoliol, a cyclic terpenoid oxide having the following structural formula:

Dihydroactinidiolide, a terpenoid oxide having the following structural formula:

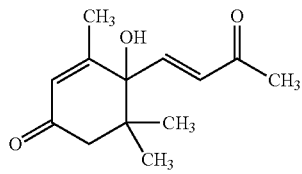 [SMILES: CC(=O)/C=C/C1(O)C(C)=CC(=O)CC1(C)C]

Elemene (a.k.s β-Elemene), a cyclic sesquiterpene having the following structural formula:

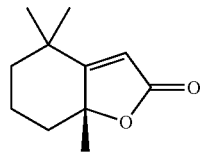

Eucalyptol/1,8-Cineole, a cyclic ether and monoterpenoid having the following structural formula:

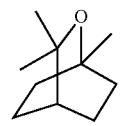

Euphol, a tetracyclic triterpene having the following structural formula:

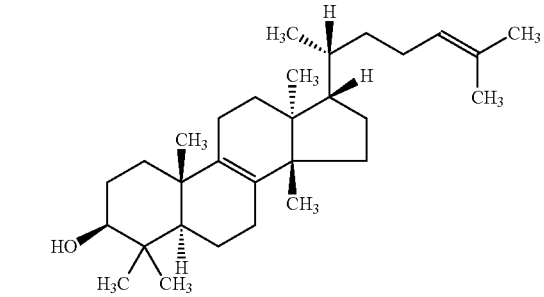 [SMILES: CC(C)=CCC[C@@H](C)[C@@H]1CC[C@]2(C)C3=C(CC[C@@]12C)[C@@]1(C)CC[C@H](O)C(C)(C)[C@@H]1CC3]

Farnesene, six closely related sesquiterpenes having the following general structural formula:

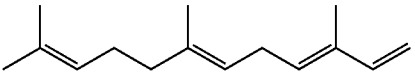

As used herein the term "farnesene" includes one of more of the six closely related compounds. Farnesol, a sesquiterpene alcohol having the following structural formula:

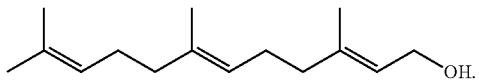 [SMILES: CC(C)=CCC/C(C)=C/CC/C(C)=C/CO]

Fenchone, a monoterpene and a ketone having the following structural formula:

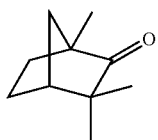

Geraniol, a monoterpenoid having the following structural formula:

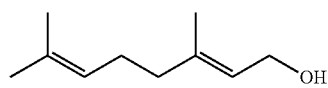

Geranyl acetate, a monoterpene with a carboxylic acid having the following structural formula:

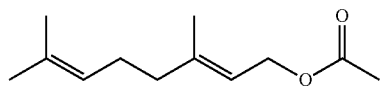

Geranylfarnesol an acyclic 25-carbon isoprenoid having the following structural formula:

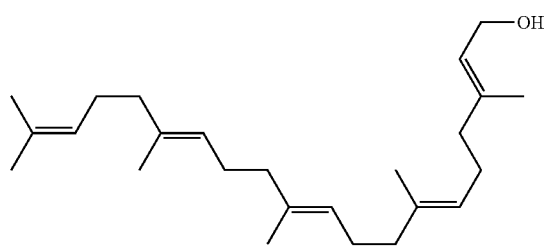 [SMILES: CC(C)=CCC/C(C)=C/CC/C(C)=C/CC/C(C)=C/CC/C(C)=C/CO]

Germacrenes a sesquiterpene having five isomers.
Germacrene A has the following structural formula:

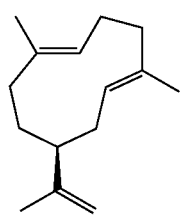

Germacrene B has the following structural formula:

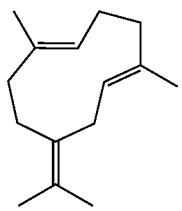

Germacrene C has the following structural formula:

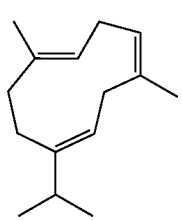

Germacrene D has the following structural formula:

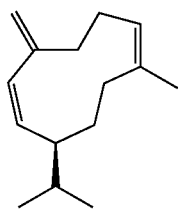

Germacrene E has the following structural formula:

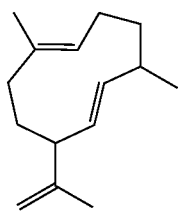

Guaia-1(10), 11-diene, a bicyclic sesquiterpene having the following structural formula:

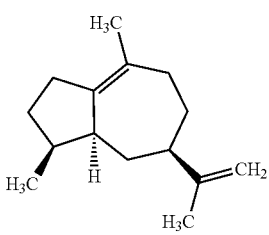

Guaiene, a bicyclic sesquiterpene wherein the α form has the following structural formula:

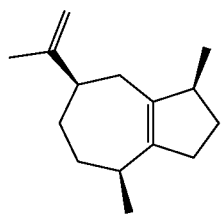

Gurjunene, a tricyclic sesquiterpene wherein the α form has the following structural formula:

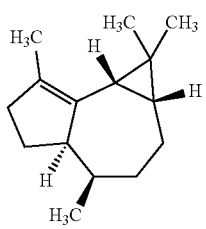

Humulene, a monocyclic sesquiterpene wherein the α form has the following structural formula:

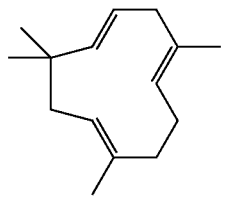

Ipsdienol, a terpene alcohol having the following structural formula:

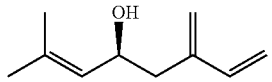

Isomyrcenol, a monoterpenoid having the following structural formula:

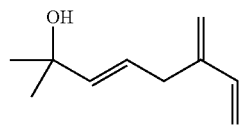

Kahweol, a diterpene having the following structural formula:

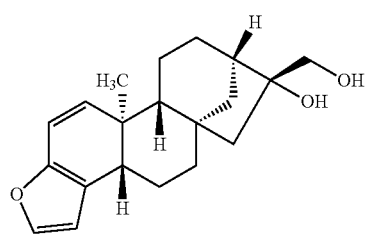

Lavandulol, a monoterpene alcohol having the following structural formula:

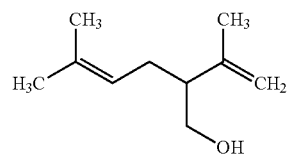

Lavandulol may be present in a racemic mixture, in the R or S form or various ratios of the R and S forms.

Limonene, a cyclic monoterpene having the following structural formula:

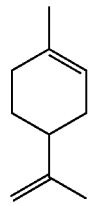

Linalool, a terpene alcohol having the following structural formula:

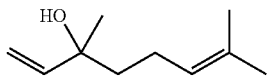

Linalyl acetate, an acetate ester of linalool having the following structural formula:

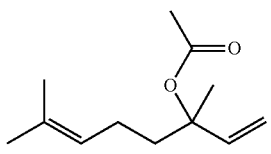

Longifolene, a tricyclic sesquiterpene having the following structural formula:

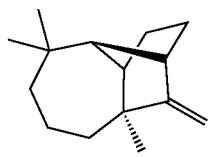

Longifolene may be present in a racemic mixture, in (+) and/or (−) enantiomers, or various ratios of the (+) and (−) enantiomers.

α-Longipinene, a bicyclic sesquiterpene having the following structural formula:

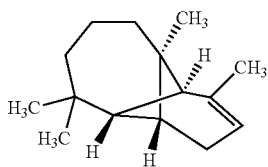

Lycopene, a tetraterpene having the following structural formula:

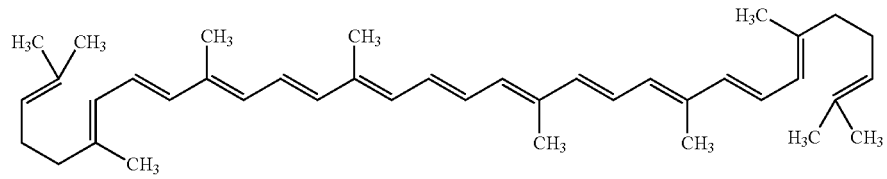 [SMILES: CC(C)=CCC/C(C)=C/C=C/C(C)=C/C=C/C(C)=C/C=C/C=C(C)/C=C/C=C(C)/C=C/C=C(\C)CCC=C(C)C]

Lycopene may also be considered a carotene.

Myrcene, a monoterpene having the following structural formula:

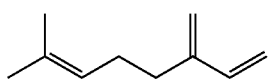

γ-Muurolene, a sesquiterpene having the following structural formula:

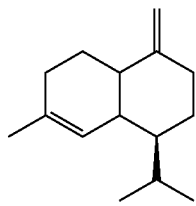

Nepetalactone, a bicyclic monoterpenoid having the following structural formula:

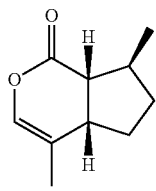

Nero, a monoterpene having the following structural formula:

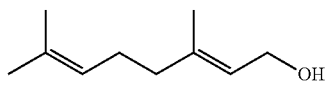

Nerolidol, a sesquiterpene with $C_{15}H_{26}O$ with cis and trans isomers. The trans-isomer has the following structural formula:

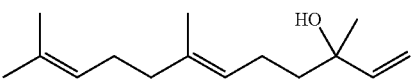 [SMILES: C=CC(C)(O)CC/C=C(\C)CCC=C(C)C]

The cis-isomer has the following structural formula:

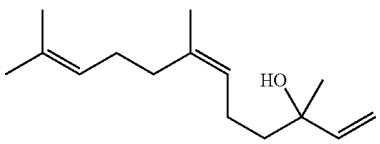 [SMILES: C=CC(C)(O)CC/C=C(/C)CCC=C(C)C]

Neryl acetate, an acetate ester of nerol having the following structural formula:

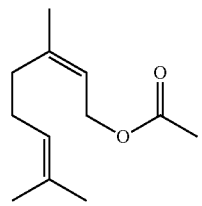

Ocimene, a group of isomeric monoterpenes. α-Ocimene has the following structural formula:

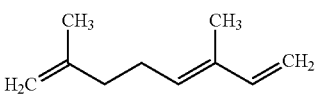

As used herein ocimene can mean any of the isomers, α-Ocimene, β-cis-Ocimene, β-trans-Ocimene, in a single pure form and/or combination.

p-Cymene, an aromatic monoterpene having the following structural formula:

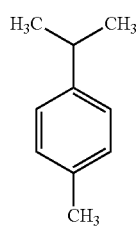

Phellandrene, a cyclic monoterpene. The α form has the following structural formula:

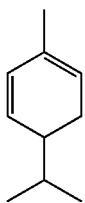

The β form has the following structural formula:

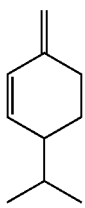

Phytol, a diterpene alcohol having the following structural formula:

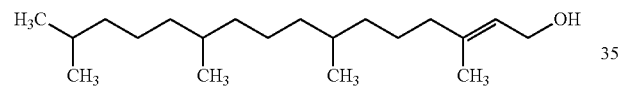

α-Pinene, a bicyclic monoterpene having the following structural formula:

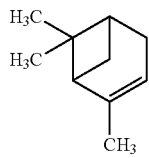

β-Pinene, a monoterpene having the following structural formula:

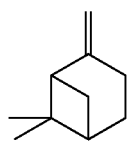

Pristimerin, a five-cyclic triterpene having the following structural formula:

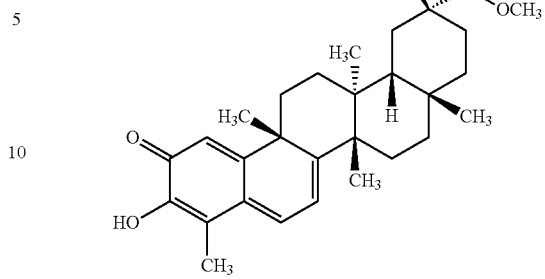

Pulegone, a cyclic monoterpene having the following structural formula:

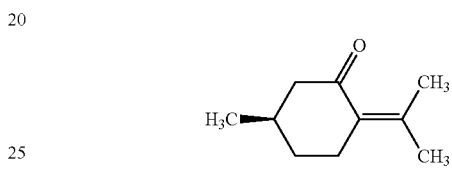

Retinol, a cyclic diterpenoid alcohol having the following structural formula:

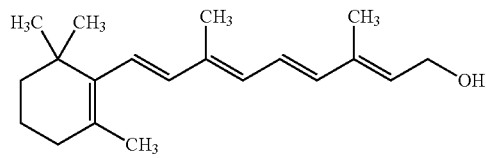 [SMILES: CC1=C(/C=C/C(C)=C/C=C/C(C)=C/CO)C(C)(C)CCC1]

Sabinene, a bicyclic monoterpene having the following structural formula:

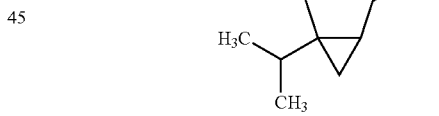

Sabinene hydrate, a cyclic monoterpene alcohol having the following structural formula:

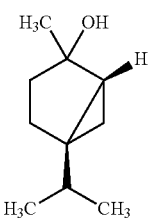

Sabinene hydrate can be present in the cis or trans form, or any ratio of the cis and trans form. Safranal, a monoterpene with an aldehyde having the following structural formula:

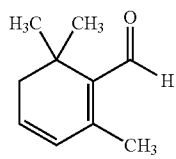

α-Selinene, a bicyclic sesquiterpene having the following structural formula:

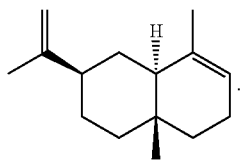

α-Sinensal, a sesquiterpenoid having the following structural formula:

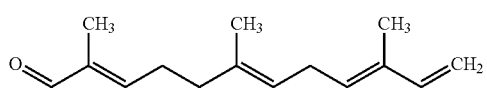 [SMILES: C=C/C(C)=C/C/C=C(\C)CC/C=C(\C)C=O]

β-Sinensal, a sesquiterpenoid having the following structural formula:

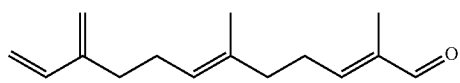 [SMILES: C=CC(=C)CC/C=C(\C)CC/C=C(\C)C=O]

Squalene, a triterpene having the following structural formula:

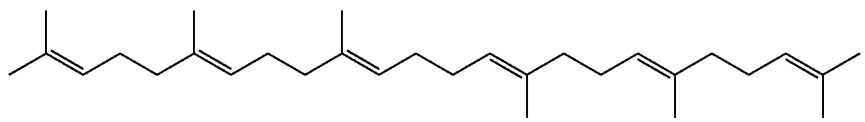 [SMILES: CC(C)=CCC/C(C)=C/CC/C(C)=C/CC/C=C(\C)CC/C=C(\C)CCC=C(C)C]

Taxadiene, a tricyclic diterpene having the following structural formula:

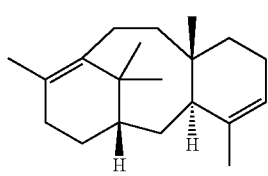 [SMILES: CC1=CCC[C@@]2(C)CCC3=C(C)CC[C@@H](C[C@H]12)C3(C)C]

Terpineol, a cyclic monoterpene alcohol having the following structural formula:

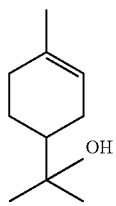

The α isomer has an isopropyl alcohol group.

Terpinen-4-ol, an isomer of terpineol having the following structural formula:

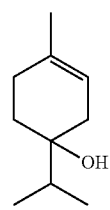

α-Terpinene, a cyclic monoterpene having the following structural formula:

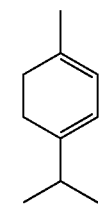

γ-Terpinene, a cyclic monoterpene having the following structural formula:

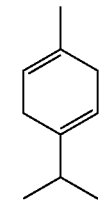

Terpinolene or Δ-Terpinene, a cyclic monoterpene with an isoprene group having the following structural formula:

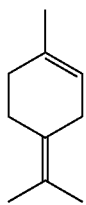

Thujone, a bicyclic monoterpene with a ketone. The α form has the following structural formula:

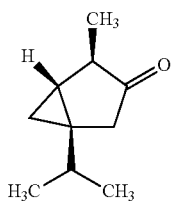

Thymol, a monoterpene phenol having the following structural formula:

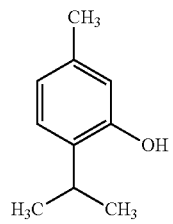

The preferred terpenes are selected from the group consisting of limonene, pinene, linalool, caryophyllene, caryophyllene oxide, nerolidol, phytol, myrcene, 1-8-cineole (aka eucalyptol), pulegone, teroineol, terpinolene, the various isomers and enantiomers thereof and combinations and mixtures of one or more of the forgoing.

Methods of Treatment

The present invention includes methods for treating mammals, preferably humans, that exhibit myotonia.

The present invention also includes methods for treating mammals, preferably humans that exhibit dystrophy. The dystrophy may be a muscular dystrophy, preferably myotonic dystrophy.

The methods of treating myotonia and/or dystrophies comprise the step of:
(i) administering an effective amount of at least one cannabinoid to a patient in need of such treatment;
(ii) administering an effective amount of at least one terpene to a patient in need of such treatment; or
(iii) administering a combination of an effective amount of at least one cannabinoid and an effective amount of at least one terpene to a patient in need of such treatment.

As used herein the term "effective amount" means the amount of an active substance, i.e., cannabinoid and/or terpene that, when administered to a subject for treating a disease, disorder, or other undesirable medical condition such as a myotonia or a dystrophy, is sufficient to have a beneficial effect with respect to that disease, disorder, or condition. The therapeutically effective amount will vary depending on the chemical identity and formulation form of the active substance, the disease or condition and its severity, and the age, weight, and other relevant characteristics of the patient to be treated. Determining the therapeutically effective amount of a given active substance is within the ordinary skill of the art. For example, a beneficial effect can include, but is not limited to, reducing the period of time a patient experiences a myotonic event. More specifically, if a patient typically experiences decreased muscle relaxation or sustained muscle contraction, lasting 2-3 minutes without treatment, an effective amount of the at least one cannabinoid, an effective amount of the at least one terpene, or an effective amount of a combination of at least one cannabinoid and at least one terpene will reduce the decreased muscle relaxation or sustained muscle contraction time by at least about 5%, about 10%, about 15%, about 20%, about 25% about 30% or more. Accordingly, a patient being treated according to the present invention would exhibit normal muscle relaxation or muscle contraction time, or a reduced muscle relaxation or muscle contraction time lasting 1 minute or less, 30 seconds or less, 15 seconds or less, 10 seconds or less or 5 seconds or less.

Another beneficial effect can include a reduction in the pain a patient with myotonia and/or a dystrophy experiences. The effect on pain can typically be measured using a visual analog scale (VAS) wherein the patient uses either a continuous horizontal or visual scale to indicate the pain he is experiencing. Typically, the scale is based on 0-10 or 0-100 wherein "0" indicates no pain and "10" or "100" indicates that pain is agonizing, unbearable or "worst imaginable". To determine the therapeutic effective amount and the benefits the present treatment provides with respect to pain reduction, the patient will indicate the pain level using a VAS prior to treatment and after an effective amount of the at least one cannabinoid, an effective amount of the at least one terpene, or an effective amount of a combination of at least one cannabinoid and at least one terpene have been administered. It is believed that the administration of an effective amount of the at least one cannabinoid, an effective amount of the at least one terpene, or an effective amount of a combination of at least one cannabinoid and at least one terpene will reduce pain by at least about 5%, about 10%, about 15%, about 20%, about 25%, about 30% or more.

A further beneficial effect can include an improvement or delayed reduction in muscle weakness as determined by the Motor Function Measure (MFM). The MFM is a generic scale which provides a measurement of the effects of muscle weakness in neuromuscular weakness in neuromuscular diseases. The MFM-32 test includes 32 assessments for patients 6 to 60 years of age and the MFM-20 test includes 20 assessments for patients under 7 years of age. More details on the MFM tests and assessments can be found at http://www.motor-function-measure.org and Berard et al., "A Motor Function Measure Scale for Neuromuscular Diseases. Construction and Validation Study," *Neuromuscular Disorders* 15 (2005) pp. 463-470 which are incorporated herein by reference. To determine the therapeutic effective amount and the benefits the present treatment provides with respect to muscle weakness, the patient may be evaluated using the MFM prior to treatment and after an effective amount of the at least one cannabinoid, an effective amount of the at least one terpene, or an effective amount of a combination of at least one cannabinoid and at least one terpene have been administered. It is believed that the administration of an effective amount of the at least one cannabinoid, an effective amount of the at least one terpene, or an effective amount of a combination of at least one cannabinoid and at least one terpene will improve the MFM score by at least about 5%, about 10%, about 15%, about 20%, about 25%, about 30% or more and/or delay the time of the expected deterioration as measured by the MFM score by at least about 5%, about 10%, about 15%, about 20%, about 25%, about 30% or more.

The administration of the effective amount of the at least one cannabinoid, the effective amount of the at least one terpene, or the effective amount of a combination of at least one cannabinoid and at least one terpene may occur about every 2 to about 3 hours, about every 4 to about 6 hours, about every 6 to about 8 hours about every 12 hours, or about every 24 hours. In certain embodiments the administration may occur once, twice three or four times a day. In one embodiment the administration of the at least one cannabinoid, the at least one terpene or the combination of at least one cannabinoid and at least one terpene occurs about every 4 to 8 hours or every 8 to 12 hours.

If a combination of the at least one cannabinoid and at least one terpene is administered, the at least one cannabinoid and at least one terpene may be administered concurrently, such as in the same dosage form, i.e., both the at least one cannabinoid and at least one terpene being present in the same tablet, capsule, liquid, suspension aerosol, or topical patch, gel, cream lotion or serum. The combined administration of the at least one cannabinoid and at least one terpene may also occur sequentially wherein either the at least on cannabinoid or the at least one terpene is administered at a first time and the at least one terpene or at least one cannabinoid is administered at a second time, and the first and second times are different. The first and second times may be separated by a few seconds such as 30 seconds, a few minutes such as about 1 to 20 minutes preferably 1 to 10 minutes and most preferably about 1 to about 5 minutes or by an hour or more. In one embodiment, the combination of the at least one cannabinoid and at least one terpene occurs with both the cannabinoid and terpene in the same dosage form so the administration is concurrent.

Although the effective amount of the at least one cannabinoid and the effective amount of the at least one terpene will vary depending upon the specific cannabinoid and terpene being administered, the route of administration, and the patient's individual characteristics such as age weight, sex, it is believed that the effective amount of the cannabinoid will range from about 0.01 mg to about 1000 mg per administration, preferably about 0.05 mg to about 800 mg per administration, and most preferably about 0.1 mg to about 700 mg per administration. It is further believed that the forgoing dosing ranges are based on the total amount of cannabinoid being administered per dose. For example, if the at least one cannabinoid comprises a mixture of THC and CBD, the total amount of cannabinoid, i.e., THC and CBD being administered should be within the aforementioned ranges. Similarly, if the at least one cannabinoid comprises a mixture of CBD, CBN and THCA, the total amount of cannabinoid, i.e., CBD, CBN and THCA being administered should be within the aforementioned ranges.

In embodiments wherein the at least one cannabinoid being administered comprises THC, it is preferred that at least a second cannabinoid such as CBD be include in the administration to counteract the psychotropic or "high" effects of THC.

It is also believed that the effective amount of the terpene will range from about 0.01 mg to about 100 mg per administration, preferably about 0.05 mg to about 50 mg per administration and most preferably about 0.1 mg to about 25 mg per administration. It is further believed that the forgoing dosing ranges are based on the total amount of terpene being administered per dose. For example, if the at least one terpene comprises a mixture of limonene and linalool, the total amount of terpene, i.e., limonene and linalool, being administered should be within the aforementioned ranges. Similarly, if the at least one cannabinoid comprises a mixture of limonene, caryophyllene, myrcene and terpinolene, the total amount of terpene, i.e., limonene, caryophyllene, myrcene and terpinolene, being administered should be within the aforementioned ranges.

The administration of the effective amount of the at least one cannabinoid, the effective amount of the at least one terpene, or the effective amount of a combination of the at least one cannabinoid and the at least one terpene, may be by any means commonly known in the art such as topical, nasal, oral, inhalation or a combination thereof. Embodiments of the invention will include combining the effective amount of the at least one cannabinoid, the effective amount of the at least one terpene, or the effective amount of the at least one cannabinoid and at least one terpene with a pharmaceutically acceptable carrier or excipient to form a pharmaceutical composition and administering the pharmaceutical composition to the patient.

In one embodiment, the method for treating myotonia or a dystrophy, preferably myotonic dystrophy, comprises the administration of 1 mg to 1000 mg, preferably 2.5 mg to 850 mg, and most preferably 3 mg to 700 mg, of one cannabinoid selected from the group consisting of THC, CBD, CBN, CBG, CBC, THCV, THCA, CBDV, CBDA, and the various isomers and enantiomers thereof.

In another embodiment, the method for treating myotonia or a dystrophy, preferably myotonic dystrophy, comprises the administration of 1 mg to 1000 mg, preferably 2.5 mg to 850 mg, and most preferably 3 mg to 700 mg, of a combination of two cannabinoids, wherein the first cannabinoid is selected from the group consisting of THC, CBD, CBN, CBG, CBC, THCV, THCA, CBDV, CBDA, the various isomers and enantiomers thereof and the second cannabinoid is selected from the group consisting of THC, CBD, CBN, CBG, CBC, THCV, THCA, CBDV, CBDA, the various isomers and enantiomers wherein the first and second cannabinoid are not the same. The ratio of first to second cannabinoid in this embodiment may range from 1:1 to 1:200, preferably 1:1.5 to 1:190 and most preferably 1:1 to 1:180.

In a further embodiment, the method for treating myotonia or a dystrophy, preferably myotonic dystrophy, comprises the administration of 0.01 mg to 1000 mg, preferably 0.05 mg to 850 mg, and most preferably 0.1 mg to 700 mg, of a combination of three cannabinoids, wherein the first cannabinoid is selected from the group consisting of THC, CBD, CBN, CBG, CBC, THCV, THCA, CBDV, CBDA, the various isomers and enantiomers thereof; the second cannabinoid is selected from the group consisting of THC, CBD, CBN, CBG, CBC, THCV, THCA, CBDV, CBDA, the various isomers and enantiomers, and the third cannabinoid is selected from the group consisting of THC, CBD, CBN, CBG, CBC, THCV, THCA, CBDV, CBDA, the various isomers and enantiomers wherein the first, second and third cannabinoids are not the same. The ratio of first to second cannabinoid in this embodiment may range from 1:1 to 1:200, preferably 1:1.5 to 1:190 and most preferably, 1:1 to 1:180 and the ratio of second cannabinoid to third cannabinoid in this embodiment may range from 1:1 to 1:200, preferably 1:1.5 to 1:190 and most preferably 1:1 to 1:180.

In one embodiment the method for treating myotonia or a dystrophy, preferably myotonic dystrophy, comprises the administration of 0.01 mg to 100 mg, preferably 0.05 mg to 50 mg, and most preferably 0.1 mg to 25 mg, of one terpene selected from the group consisting of limonene, pinene, linalool, caryophyllene, caryophyllene oxide, nerolidol, phytol, myrcene, 1-8-cineole, pulegone, teroineol, terpinolene, the various isomers and enantiomers thereof.

In another embodiment, the method for treating myotonia or a dystrophy, preferably myotonic dystrophy, comprises the administration of 0.01 mg to 100 mg, preferably 0.05 mg to 50 mg, and most preferably 0.1 mg to 25 mg, of a combination of two terpenes, wherein the first terpene is selected from the group consisting of limonene, pinene, linalool, caryophyllene, caryophyllene oxide, nerolidol, phytol, myrcene, 1-8-cineole, pulegone, teroineol, terpinolene, the various isomers and enantiomers thereof and the second terpene is selected from the group consisting of limonene, pinene, linalool, caryophyllene, caryophyllene oxide, nerolidol, phytol, myrcene, 1-8-cineole, pulegone, teroineol, terpinolene, the various isomers and enantiomers thereof wherein the first and second terpene are not the same. The ratio of first to second terpene in this embodiment may range from 1:5 to 5:1, preferably 1:4 to 4:1 and most preferably 1:3 to 3:1.

In a further embodiment, the method for treating myotonia or a dystrophy, preferably myotonic dystrophy, comprises the administration of 0.01 mg to 100 mg, preferably 0.05 mg to 50 mg, and most preferably 0.1 mg to 25 mg, of a combination of three terpenes, wherein the first terpene is selected from the group consisting of limonene, pinene, linalool, caryophyllene, caryophyllene oxide, nerolidol, phytol, myrcene, 1-8-cineole, pulegone, teroineol, terpinolene, the various isomers and enantiomers thereof, the second terpene is selected from the group consisting of limonene, pinene, linalool, caryophyllene, caryophyllene oxide, nerolidol, phytol, myrcene, 1-8-cineole, pulegone, teroineol, terpinolene, the various isomers and enantiomers thereof, the third terpene is selected from selected from the group consisting of limonene, pinene, linalool, caryophyllene, caryophyllene oxide, nerolidol, phytol, myrcene, 1-8-cineole, pulegone, teroineol, terpinolene, the various isomers and enantiomers thereof, wherein the first, second and third terpenes are not the same. The ratio of first to second terpene in this embodiment may range from 1:5 to 5:1, preferably 1:4 to 4:1 and most preferably 1:3 to 3:1 and the ratio of second terpene to third terpene in this embodiment may range from 1:5 to 5:1, preferably 1:4 to 4:1 and most preferably 1:3 to 3:1.

In one embodiment the method for treating myotonia or a dystrophy, preferably myotonic dystrophy, comprises the administration of:
(i) 0.01 mg to 1,000 mg, preferably 0.05 mg to 850 mg, and most preferably 0.1 mg to 700 mg, of one cannabinoid selected from the group consisting of THC, CBD, CBN, CBG, CBC, THCV, THCA, CBDV, CBDA, the various isomers and enantiomers thereof and
(ii) optionally 0.01 mg to 100 mg, preferably 0.05 mg to 50 mg, and most preferably 0.1 mg to 25 mg, of one terpene selected from the group consisting of limonene, pinene, linalool, caryophyllene, caryophyllene oxide, nerolidol, phytol, myrcene, 1-8-cineole, pulegone, teroineol, terpinolene, the various isomers and enantiomers thereof.

In another embodiment, the method for treating myotonia or a dystrophy, preferably myotonic dystrophy, comprises the administration of:
(i) 0.01 mg to 1000 mg, preferably 0.05 mg to 850 mg, and most preferably 0.1 mg to 700 mg, of a combination of two cannabinoids, wherein the first cannabinoid is selected from the group consisting of THC, CBD, CBN, CBG, CBC, THCV, THCA, CBDV, CBDA, the various isomers and enantiomers thereof and the second cannabinoid is selected from the group consisting of THC, CBD, CBN, CBG, CBC, THCV, THCA, CBDV, CBDA, the various isomers and enantiomers wherein the first and second cannabinoid are not the same; and
(ii) optionally 0.01 mg to 100 mg, preferably 0.05 mg to 50 mg, and most preferably 0.1 mg to 25 mg, of one or more terpenes selected from the group consisting of limonene, pinene, linalool, caryophyllene, caryophyllene oxide, nerolidol, phytol, myrcene, 1-8-cineole, pulegone, teroineol, terpinolene, the various isomers and enantiomers thereof;

wherein the ratio of first to second cannabinoid in this embodiment may range from 1:1 to 1:200, preferably 1:1.5 to 1:190 and most preferably 1:1 to 1:180.

In a further embodiment, the method for treating myotonia or a dystrophy, preferably myotonic dystrophy, comprises the administration of:
(i) 0.01 mg to 1,000 mg, preferably 0.05 mg to 850 mg, and most preferably 0.1 mg to 700 mg, of a combination of three cannabinoids, wherein the first cannabinoid is selected from the group consisting of THC, CBD, CBN, CBG, CBC, THCV, THCA, CBDV, CBDA, the various isomers and enantiomers thereof; the second cannabinoid is selected from the group consisting of THC, CBD, CBN, CBG, CBC, THCV, THCA, CBDV, CBDA, the various isomers and enantiomers, and the third cannabinoid is selected from the group consisting of THC, CBD, CBN, CBG, CBC, THCV, THCA, CBDV, CBDA, the various isomers and enantiomers wherein the first, second and third cannabinoids are not the same;
(ii) optionally 0.01 mg to 100 mg, preferably 0.05 mg to 50 mg, and most preferably 0.1 mg to 25 mg, of one or more terpenes selected from the group consisting of limonene, pinene, linalool, caryophyllene, caryophyllene oxide, nerolidol, phytol, myrcene, 1-8-cineole, pulegone, teroineol, terpinolene, the various isomers and enantiomers thereof;

wherein the ratio of first to second cannabinoid in this embodiment may range from 1:1 to 1:200, preferably 1:1.5 to 1:190 and most preferably 1:1 to 1:180 and the ratio of second cannabinoid to third cannabinoid in this embodiment may range from 1:1 to 1:200, preferably 1:1.5 to 1:190 and most preferably 1:1 to 1:180.

In certain preferred embodiments, the methods of the present invention comprise the administration, preferably the oral administration, of a tablet, capsule or liquid (i.e., solution or suspension) comprising a combination of THC and CBD in a ratio of about 1:1 to 1:200, preferably 1:1.5 to 1:190 and most preferably 1:1 to 1:180. The oral administration will occur once, twice, three or four times a day, preferably two or three times a day. Each administration will comprise: (i) about 1-100 mg of THC, preferably 2-75 mg of THC and most preferably 5-50 mg of THC and (ii) about 1-1000 mg of CBD, preferably 2-850 mg of CBD and most preferably 5-700 mg of CBD. The target of the oral administration is to obtain a steady state plasma level of THC ranging from 0.25 ng/mL to 25 ng/mL, preferably 0.5 ng/mL to 17.5 ng/mL and most preferably 1 ng/mL to 12.5 ng/mL, and a steady state plasma level of CBD greater than 0.5 ng/mL, preferably greater than 1 ng/mL and most preferably greater than 3 ng/mL. The foregoing administrations and target pharmacokinetic steady state plasma levels will be effective in the treatment of myotonia or a dystrophy, preferably myotonic dystrophy. The foregoing administrations will reduce the pain associated with the myotonia or dystrophy, improve the muscle movement and provide an overall improvement in the quality of a patient's life. In the case of myotonia and myotonic dystrophy in particular, the administration will enable a quicker relaxation of a patient's muscles following contraction than without administration and thereby should improve muscle movement and improve the patient's quality of life.

Compositions

The present invention includes pharmaceutical compositions that are useful in the treatment of myotonia and/or dystrophies. The pharmaceutical compositions in accordance with the present invention include:
  (i) an effective amount of at least one cannabinoid and at least one pharmaceutically acceptable carrier or excipient;
  (ii) an effective amount of at least one terpene and at least one pharmaceutically acceptable carrier or excipient; or
  (iii) an effective amount of at least one cannabinoid, an effective amount of at least one terpene and at least one pharmaceutically acceptable carrier or excipient.

The pharmaceutically acceptable carrier(s) or excipient(s) are known in the art and their selection will depend upon the route of administration.

Topical Compositions

One embodiment of the invention is directed to topical compositions for the administration of the at least one cannabinoid, the at least one terpene, or the combination of at least one cannabinoid and at least one terpene. The topical compositions include occluded forms, such as matrix and reservoir patches, and unoccluded forms, such as gels, creams, lotions, ointments, and serums, as wells as topical foams and mousses.

Matrix patches in accordance with the present invention comprise at least one cannabinoid, the at least one terpene or the combination of at least one cannabinoid and at least one terpene homogeneously blended in a solid or semisolid polymer carrier together with other additives (e.g., permeation enhancers, plasticizers, viscosity reducing agent, and the like). The general structure and fabrication of matrix patches are well known in the art. In a preferred embodiment, the matrix patch comprises an occlusive backing that is impermeable to the at least one cannabinoid, the at least one terpene or the combination of at least one cannabinoid and at least one terpene and defines the face or top surface of the patch and a solid or semisolid matrix layer comprised of a homogeneous blend of the at least one cannabinoid, the at least one terpene or the combination of at least one cannabinoid and at least one terpene and one or more skin permeation enhancers.

The polymeric carrier may be adhesive or nonadhesive. When it is a pressure sensitive adhesive the basal surface of the matrix layer may be used to affix the patch to the skin. When it is not, other means such as an underlying adhesive layer, a peripheral adhesive layer, an adhesive overlay, or straps may be used to affix the patch to the skin.

Examples, without limitation, of specific polymers that may be used as the carrier are polyacrylates, polymethacrylates, natural and synthetic rubbers, silicone rubbers and elastomers, polyolefins, vinyl copolymers, urethanes, nylons, polyesters, polyethers, and the like.

The skin permeation enhancer(s) that are included in the matrix enhance the level of skin flux of cannabinoid and/or terpene. Examples of permeation enhancers that may be used in compositions of the present invention include, but are not limited to, fatty acids, fatty acid esters, fatty alcohols, fatty acid esters of lactic acid or glycolic acid, glycerol tri-, di- and monoesters, triacetin, short chain alcohols, amine oxides and mixtures thereof. Particular examples of permeation enhancers include oleyl alcohol, lauryl alcohol, isopropyl myristate, oleyl oleate, levulinic acid, ethanol, glycerol monooleate, methyl laurate, sorbitain monooleate, triacetin, aloe vera oil, benzothonium chloride, cetyl dimethylamine oxide, cetyl alcohol, cetyl lactate, cocamidopropyl betaine, cocoamine oxide diethanolamine, dimethyloctylamine oxide, 2-dodecoxyethyldimethylamine oxide, dimethyl-decylamine oxide, dimethylhexadecylamine oxide, dimethyl-tetradecylamine oxide, dimethyl isosorbide, dipropylene glycol, ethyl hexyl lactate, glycolic acid, 3-dodecoxy-2-hydroxypropyldi(3-hydroxypropyl)amine oxide, lactic acid, lauramine oxide, lauryl betaine, lauryl lactate, lauryl laurate, isopropyl palmitate, macrogol 15 hydroxystearate (Solutol HS 15), menthol, menthyl lactate, myristyl alcohol, myristal lactate, octyldodecanol, octyl salicylate, oleamine oxide, oleic acid, oleyl betaine, oleyldi(2-hydroxyethyl) amine oxide, PEG 1000, pentadecalactone, propylene glycol, salicylic acid, stearyl alcohol, stearyl lactate, 3,6,9-trioxaheptadecyldiethylamine oxide, di(2-hydroxyethyl)-tetradecylamine oxide, triethanolamine triacetate and combinations thereof. Other permeation enhancers useful with the present invention may be found in U.S. Patent Application Publication No. 2007/0269379, which is incorporated in its entirety herein by reference. Preferred permeation enhancers include oleyl alcohol, lauryl alcohol, isopropyl myristate, oleyl oleate, levulinic acid, glycerol monooleate, methyl laurate, sorbitain monooleate, triacetin, cetyl alcohol, cetyl lactate, dimethyl isosorbide, dipropylene glycol, ethyl hexyl lactate, glycolic acid, lauramine oxide, lauryl betaine, lauryl lactate, lauryl laurate, isopropyl palmitate, myristyl alcohol, myristal lactate, octyl salicylate, oleamine oxide, oleic acid, oleyl betaine, salicylic acid, stearyl alcohol, stearyl lactate, triethanolamine triacetate and combinations thereof. The permeation enhancer will usually constitute 1 to 20 wt % of the matrix, more usually 5 to 15 wt % of the matrix.

The patches of the invention may be manufactured by conventional techniques used in transdermal drug delivery device art. For instance, the at least one cannabinoid, the at least one terpene or the combination of at least one cannabinoid and at least one terpene, carrier, and enhancer(s) may be mixed in the desired proportions to form a homogeneous mixture and cast or otherwise applied to a backing layer, by lamination to a release liner layer.

Reservoir patches in accordance with the present invention may comprise a gelled liquid solution or suspension containing at least one cannabinoid, at least one terpene or a combination of at least one cannabinoid and at least one terpene and an enhancer within a carrier or be in the form of a fibrous body impregnated with the drug in the carrier. In addition to the reservoir, the device includes means for maintaining the reservoir in diffusional communication with the skin. Such means include a carrier which is also an adhesive, a separate basal adhesive layer underlying the reservoir, a peripheral ring of adhesive that is interconnected to the reservoir, an adhesive overlay for the reservoir, and straps. Preferably the means is either an adhesive carrier or a separate underlying adhesive layer.

In addition to the reservoir and affixation means, the patches may further include a backing that overlies the reservoir and protects the reservoir and/or prevents back-diffusion of the at least one cannabinoid, the at least one terpene or the combination of at least one cannabinoid and at least one terpene and enhancer from the reservoir, one or more structural layers to provide the device with appropriate mechanical properties, and/or a release liner layer that underlies the reservoir and which is removed prior to use and means for affixing the device to the skin.

The carrier or vehicle is permeable to the at least one cannabinoid, the at least one terpene or the combination of at least one cannabinoid and at least one terpene and the permeation enhancer. Preferably, the carrier is a fluid (e.g., liquid, gel, emulsion, suspension). It may be aqueous or nonaqueous. Examples of fluid carriers that may be used are alcohols such as ethanol, alcohol-water mixtures, and low molecular weight polymers such as polyethylene glycol. Ethanol is preferred and also provides permeation enhancement. In the case of ethanol, the carrier normally constitutes 20% to 70% by volume of the reservoir, more usually 40% to 60%, and preferably approximately 50%. Alternatively, the carrier may be a solid or semisolid matrix such as a pressure-sensitive adhesive.

The reservoir patches may contain a permeation enhancer as discussed above. The reservoir may also contain amounts of other materials such as gelling agents and anti-irritants. Glycerin is a preferred anti-irritant and may be present at 5% to 50%, preferably 20% to 30% by volume. The use of glycerin as an anti-irritant is described in U.S. Pat. No. 4,855,294.

The reservoir patches may be manufactured by conventional techniques used in the transdermal drug delivery device art. For instance, at least one cannabinoid, at least one terpene or a combination of at least one cannabinoid and at least one terpene, a permeation enhancer and carrier may be mixed in the desired proportions to form a homogeneous mixture and cast or otherwise applied to a backing layer, followed by lamination to a release liner layer. If a separate basal adhesive layer is desired, it may be cast onto the release liner layer prior to such lamination.

The patches will be typically designed to be worn for 0.5 to 14 days, more preferably 1 to 7 days, and most preferably 1-3 days. The thickness of the matrix layer may be 0.01 to 1 mm, more preferably 0.025 to 0.25 mm. The thickness of the reservoir will usually be about 0.01 to 5 mm, more usually 0.03 to 2 mm. The area of the patch in diffusional contact with the skin may be between 1 and 150 cm$^2$, more preferably 5 and 100 cm$^2$, and most preferably 10 and 75 cm$^2$. The required dosing may be supplied by a single device or by a plurality of devices applied to the skin.

A further embodiment of the present invention is directed to topical gels, creams, lotions, ointments, serums, foams, and mousses of at least one cannabinoid, at least one terpene or combination of at least one cannabinoid and at least one terpene (collectively "unoccluded topical dosage forms").

In addition to the at least one cannabinoid, the at least one terpene or the combination of at least one cannabinoid and at least one terpene, the unoccluded topical dosage forms may contain a penetration enhancer as discussed above. Depending upon the specific topical dosage form, i.e., serum, cream or foam, the topical dosage form of the present invention may also include further additives such as solvents, film forming/polymeric agents, viscosity increasing agents, emulsifiers, antioxidants, preservatives, pH adjusting agents, propellants and combinations of the foregoing. The unoccluded topical dosage forms may be uniform compositions, emulsions, such as oil-in-water or water-in-oil emulsions, or liposomal compositions.

The unoccluded topical dosage forms of the present invention may include any suitable solvent. Preferably, the solvent may include water and/or one or more organic compounds, e.g., esters, alcohols, ketones, aldehydes, fatty acids, partially or fully esterified fatty acids, wherein the structures are cyclic, non-cyclic (e.g., alkyl), alicyclic (i.e., a bridged ring compound), or aromatic, as well as organic compounds having combinations of these functional groups. Specific examples of solvents that may be employed are water, methanol, ethanol, isopropyl alcohol, acetone, hexane, butyl alcohol, ethyl acetate, polyethylene glycol, propylene glycol, ethylene glycol, triethylene glycol, glycerin, 1,3-propane diol, 2-methyl-1,3-propane diol, glycerol ricinoleate, mineral oil, peanut oil, corn oil, cottonseed oil, sesame oil or a combination thereof. The solvent may be employed in any suitable amount. Typically, the solvent can be present in the unoccluded topical composition in about 1.0 wt % to about 95.0 wt % based upon the total weight of the unoccluded topical dosage form, preferably about 3.0 wt % to about 85 wt % based upon the total weight of the unoccluded topical composition and most preferably about 5.0 wt % to about 75 wt % of the total weight of the unoccluded topical composition.

The unoccluded topical dosage forms of the present invention also may optionally include a film-forming/polymeric agent. The film-forming/polymeric agent may enhance the adherence of the composition to the patient's skin and improve the composition's resistance to washing off or rubbing off. Film-forming/polymeric agents are preferably soluble or miscible with the at least one cannabinoid, the at least one terpene or the combination of at least one cannabinoid and at least one terpene, solvent and/or penetration enhancer. The unoccluded topical dosage forms of the present invention typically comprises from about 0.001 wt % to about 25 wt %, preferably about 0.005 wt % to about 15 wt % and most preferably about 0.010 wt % to about 10 wt % based upon the total weight of the unoccluded topical composition of the film-forming/polymeric agents. Some examples of film-forming/polymeric agents that may be used in compositions of the present invention are polyalkenes, oleophilic copolymers of vinylpyrrolidone, acrylic copolymers, polyethylene glycol derivative, polyolefins, polyurethanes and mixtures thereof.

Examples of polyalkenes that may be included in the topical dosage forms of the present invention are polyethylenes having a molecular weight ranging from about 300 to about 3000 (available as PERFORMALENE® from New Phase Technologies, Piscataway, N.J.); polyisobutylenes (available as VISTANEX™ from Exxon Chemical Company, Houston, Tex.); polyisobutenes (available as PRESPERSE™ from Sumitomo Corp.); polydecenes (SILKFLO™ available from Amoco); and hydrogenated polyisobutenes (PANALANE® available from Lipo Chemicals, Inc., Paterson, N.J.).

Oleophilic copolymers of vinylpyrollidone suitable for use in the topical dosage forms of the present invention may be copolymers of polyvinylpyrrolidone (PVP) and long chain alpha olefins, including, but not limited to, PVP/eicosene copolymers (GANEX® V-220 and V-220F), and tricontanyl PVP copolymers (GANEX®) available from Ashland, formerly International Specialty Products, Wayne, N.J.

Examples of acrylic copolymers that may be used in the topical dosage forms of the present invention include acrylic copolymers having long ($C_8$-$C_{30}$) alkyl chains to enhance their oleophilicity, such as acrylate/octylacrylamide copolymers (available as DERMACRYL® from Akzo Nobel). An example of a polyethylene glycol derivative that may be used as a film forming agent in compositions of the present invention is a polyethylene glycol derivative of Beeswax (ESTOL® E04BW-3752, E06BW-3753 or E03BW-3751 formerly available from Unichema, Wilmington, Del. and currently available from Croda under the trade name CITHROL®). Examples of polyolefins that may be used as a film forming agent in compositions of the present invention are fatty acid ester/fatty acid anhydride grafted polyolefins wherein the esters and anhydrides are derived from $C_{12}$-$C_{22}$ fatty acid moieties, for example, $C_{30}$-$C_{38}$ olefin/isopropyl maleate/maleic anhydride copolymer (PERFORMA™ V 1608, available from New Phase Technologies, Piscataway, N.J.).

The film forming/polymeric agents may water-insoluble, oleophilic, water-resistant, or water-soluble.

The unoccluded topical dosage forms of the present invention may also contain viscosity enhancing agents that thicken, gel or harden the composition. An unoccluded topical dosage forms in accordance with the present invention, such as a topical gel, typically comprises from about 0.001 wt % to about 50 wt % of the viscosity enhancing agent, preferably about 0.005 wt % to about 40 wt % and most preferably about 0.01 wt % to about 25 wt % based upon the total weight of the unoccluded topical composition. Exemplary viscosity enhancing agents include organic materials such as natural or synthetic waxes, $C_{12}$-$C_{60}$ alcohols, $C_{12}$-$C_{60}$ acids, alpha-hydroxy fatty acids, polyhydroxy fatty acid esters, polyhydroxy fatty acid amides, and inorganic/organic materials such as metal ester complexes containing zinc, calcium, aluminum or magnesium, fumed silicas, and organoclays. Additional viscosity enhancing agents include polyol polyesters, glyceryl esters, polyglyceryl esters and polysiloxanes that are a solid or semi-solid at ambient temperature.

Specific examples of viscosity enhancing agents that may be included in the unoccluded topical dosage forms of the present invention include $C_{12}$-$C_{60}$ alcohols, preferably $C_{16}$-$C_{22}$ fatty alcohols, such as cetyl alcohol, stearyl alcohol, behenyl alcohol and mixtures thereof. Other suitable viscosity enhancing agents include $C_{12}$-$C_{60}$ acids, preferably $C_{16}$-$C_{22}$ fatty acids, such as palmitic acid, stearic acid, behenic acid, oleic acid, linoleic acid, myristic acid, ricinoleic acid, eurcic acid, lauric acid, isostearic acid and mixtures thereof. Further suitable viscosity enhancing agents that may be used herein are alpha-hydroxy fatty acids, including 12-hydroxystearic acid, 12-hydroxylauric acid, 16-hydroxyhexadecanoic acid and mixtures thereof. Additional examples of suitable fatty acids are further described in Klofta et al., U.S. Pat. No. 7,449,613, Hofrichter, et al., U.S. Pat. No. 5,429,816 and Motley, U.S. Pat. No. 5,552,136, disclosure of each is incorporated in its entirety herein by reference.

Waxes are also suitable for use as viscosity enhancing agents in unoccluded topical dosage forms of the present invention. Natural waxes may include, but are not limited to, carnauba, ozokerite, beeswax, candelilla, paraffin, ceresin, esparto, ouricuri, rezowax and other known mined and mineral waxes. Synthetic waxes may include, but are not limited to, paraffin waxes and microcrystalline waxes.

Additional viscosity enhancing agents that may be used include polyhydroxy fatty acid esters, polyhydroxy fatty acid amides and mixtures thereof. Preferred esters and amides will have three or more free hydroxy groups on the polyhydroxy moiety and are typically nonionic in character. Because of the possible skin sensitivity of those using articles to which the unoccluded topical dosage form is applied, these esters and amides should also be relatively mild and non-irritating to the skin. Suitable polyhydroxy fatty acid esters and polyhydroxy fatty acid amides are disclosed in Roe et al., U.S. Pat. No. 5,643,588, the disclosure of which is incorporated in its entirety herein by reference.

Still further viscosity enhancing agents that may be included in the unoccluded topical dosage forms of the present invention are gelling agents. Gelling agents are materials that can swell or expand when in contact with water. Examples of gelling agents that may be used in the present invention include swellable polymers, also known as osmopolymers or hydrogels as previously described. The swellable polymer can be non-cross-linked or lightly cross-linked. The cross-links can be covalent or ionic bonds with the polymer possessing the ability to swell in the presence of fluid, and when cross-linked it will not be dissolved in the fluid. The polymer can be of plant, animal or synthetic origin. Polymeric materials useful for the present purpose include polyhydroalkylcellulose having a molecular weight greater than 50,000, such as hydroxyl propylmethylcellulose (METHOCEL® K 100M available from Dow Chemical); poly(hydroxyalkylmethacrylate) having a molecular weight of from 5,000 to 5,000,000; poly(vinylpyrrolidone) having a molecular weight of from 100,000 to 3,000,000; anionic and cationic hydrogels; poly(electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; a water-swellable copolymer produced by a dispersion of a finely divided copolymer of maleic anhydride with styrene, ethylene, propylene, or isobutylene; a water-swellable polymer of N-vinyl lactams and the like.

Other gelling agents useful in the unoccluded topical dosage forms of the present invention include pectin having a molecular weight ranging from 30,000 to 300,000; polysaccharides such as agar, acacia, karaya, tragacanth, algins and guar; CARBOPOL®, an acrylic acid polymer, a carboxyvinyl polymer, sometimes referred to as carboxypolymethylene, a polymer of acrylic acid cross-linked with a polyallyl ether of sucrose, as described in U.S. Pat. Nos. 2,798,053 and 2,909,462 and available as CARBOPOL® 934, 940 and 941, and its salt derivatives; polyacrylamides; water-swellable indene maleic anhydride polymers; GOODRITE® polyacrylic acid having a molecular weight of 80,000 to 200,000; POLYOX® polyethylene oxide polymers having a molecular weight of 100,000 to 7,000,000; starch graft copolymers; AQUA-KEEP® acrylate polymers with water absorbability of about 400 times its original weight; diesters of polyglucan; a mixture of cross-linked polyvinyl alcohol and poly(N-vinyl-2-pyrrolidone); poly (ethylene glycol) having a molecular weight of 4,000 to 100,000. Representative polymers possessing gelling properties are described in U.S. Pat. Nos. 6,419,954, 4,915,949, 4,327,725, 4,207,893 and in *Handbook of Common Polymers*, by Scott and Roff, published by Cleveland Rubber Company, Cleveland, Ohio.

Examples of inorganic viscosity enhancing agents that may be included in the unoccluded topical dosage forms of the present invention include treated and untreated fumed silicas such as those available from Cabot Corp., Tuscola, Ill. under the trade designations CAB-O-SIL M5 and MS-55. Exemplary surface-treated fumed silicas are also available from Cabot Corp., Tuscola, Ill. under the trade designations TS-720 and TS-610.

Suitable clays such as hectorite and smectite may also be used as viscosity enhancing agents in unoccluded topical dosage forms of the present invention.

Hydrogenated vegetable oils such as cocoa butter, shea butter and mixtures thereof may also be used as viscosity enhancing agents in unoccluded topical dosage forms of the present invention.

Suitable petroleum-based emollients may also be used as viscosity enhancing agents in unoccluded topical dosage forms of the present invention. Examples of suitable petroleum-based emollients that may be used include petrolatums, i.e., hydrocarbons or mixtures of hydrocarbons; particularly preferred are hydrocarbons having chain lengths of from $C_{10}$ to $C_{100}$. Petroleum-based emollients within this chain length range include mineral oil and petrolatum. Mineral oil usually refers to less viscous mixtures of hydrocarbons having from 10 to 30 carbon atoms, though the hydrocarbon molecular weight distribution may vary. Since the lower molecular weight hydrocarbons can cause irritation in some individuals, mineral oils having a small percentage of lower molecular weight hydrocarbons are preferred. Petrolatum usually refers to more viscous mixtures of hydrocarbons of higher molecular weight hydrocarbons. Petrolatum and mineral oil are preferred skin conditioning agents for compositions of the present invention due to their ability to protect the skin from harmful or irritating stimuli. Petrolatum is particularly preferred because of its good barrier properties.

The unoccluded topical dosage forms of the present invention may also contain humectants. Unoccluded topical dosage forms in accordance with the present invention typically comprises from about 0.001 wt % to about 30 wt % of a humectant, preferably about 0.005 wt % to about 20 wt % and most preferably about 0.01 wt % to about 10 wt % based upon the total weight of the unoccluded topical composition. Examples of compounds that may be used as humectants in compositions of the present invention are esters of polyhydroxy alcohols. This type of ester may include glyceryl esters including glycerides and derivatized glycerides, polyglyceryl esters, and glycolic esters. Glyceryl esters are derived from glycerin, its derivatives and one or more carboxylic acid moieties. Non-limiting examples include various $C_1$-$C_{30}$ mono-, di- or tri-esters of glycerin and derivatives thereof, such as mono-, di-, tri-glycerides, acetoglycerides, and ethoxylated glycerides. Exemplary glyceryl esters include glyceryl behenate, glyceryl oleate, glyceryl stearate, glyceryl palmitate, glyceryl distearate, glyceryl dipalmitate and the like. Polyglyceryl esters having $C_{12}$-$C_{22}$ acid moieties are also suitable for use herein. Non-limiting examples include polyglyceryl-4 isostearate, polyglyceryl-3 oleate, diglyceryl monooleate, tetraglyceryl monooleate and the like. Glycolic esters are derived from $C_2$-$C_6$ glycols, including ethylene glycol, propylene glycol, butylene glycol, hexylene glycol and derivatives thereof, and one or more carboxylic acid moieties having $C_1$-$C_{30}$ chains. Specific examples of glycolic esters include polyethylene glycols (PEGs), such as PEG-2, PEG-3, PEG-30 and PEG-50, and polypropylene glycols (PPGs), such as PPG-9, PPG-12, PPG-15, PPG-17, PPG-20, PPG-26, PPG-30 and PPG-34.

The unoccluded topical dosage forms of the present invention may also contain emulsifiers or dispersing agents such as anionic, cationic and nonionic surfactants. Unoccluded topical dosage forms in accordance with the present invention typically comprises from about 0.001 wt % to about 15 wt % of an emulsifier or dispersing agent, preferably about 0.005 wt % to about 10 wt % and most preferably about 0.01 wt % to about 5 wt % based upon the total weight of the unoccluded topical composition. Nonionic surfactants are preferred because of their low level of irritation to skin. Typical nonionic surfactants are monoglycerides such as glyceryl monostearate and the like; sorbitan aliphatic esters such as sorbitan monolaurate and the like; sucrose aliphatic esters; polyoxyethylene aliphatic esters such as polyoxyethylene stearate; and polyoxyethylene higher alcohol ethers such as polyoxyethylene cetyl ether, polyoxyethylene oleyl ether, polyoxyethylene fatty ethers and the like.

The unoccluded topical dosage forms of the present invention may also contain an antioxidant to minimize or prevent the oxidation process and enhance the shelf life of the composition. Unoccluded topical dosage forms in accordance with the present invention typically comprises from about 0.001 wt % to about 25 wt % of an anti-oxidant, preferably about 0.005 wt % to about 15 wt % and most preferably about 0.01 wt % to about 10 wt % based upon the total weight of the unoccluded topical composition. Antioxidants useful herein should preferably be mild and non-irritating. Antioxidants from natural sources are preferred, such as Vitamin E and its derivatives, including tocopherol, tocopherol acetate, mixed tocopherols (available as COVI-OX T-50 or T-70 from Henkel Corp, Ambler, Pa.), and the like or butylated hydroxytoluene, butylated hydroxyanisole, sodium pyrosulfite, acetone sodium bisulfate and the like. Some of these antioxidants are also useful as skin antioxidants, which minimizes the wrinkles and dullness of the skin and provides a more youthful looking and firmer textured skin.

The unoccluded topical dosage forms of the present invention may also contain a preservative to prevent bacterial growth and odors thereof, particularly in compositions having a relatively high water content. Unoccluded topical dosage forms in accordance with the present invention typically comprise from about 0.001 wt % to about 10 wt % of a preservative, preferably about 0.005 wt % to about 5 wt % and most preferably about 0.01 wt % to about 2.5 wt % based upon the total weight of the unoccluded topical composition. Suitable preservatives include propyl paraben, methyl paraben, benzyl alcohol, benzalkonium chloride, tribasic calcium phosphate, phenoxyethanol, or acids such as citric, tartaric, maleic, lactic, malic, benzoic, salicylic, and the like.

The unoccluded topical dosage forms of the present invention may include an acid or base to adjust the pH of the composition to the desired or optimal range. Examples of compounds typically used to adjust the pH of topical compositions include oleic acid, hydrochloric acid, citric acid, lactic acid, tartaric acid, glacial acetic acid, sodium hydroxide or the like. Depending upon the form in which the unoccluded topical dosage form is applied, i.e., gel, serum or cream, and the location, the desired final pH value of the composition may vary, however, it is generally preferred that the composition range from a pH of about 5.0 to about 8.5, preferably about 6 to about 8.0, and most preferably about 6.5 to about 7.5.

In order to increase the stability of the unoccluded topical dosage forms of the present invention, it may be necessary to add a chelating agent. Suitable chelating agents may include ethylenediaminetetraacetic acid (EDTA) and its derivatives, thioglycolic acid, thiolactic acid, thioglycerol, and the like.

A fragrance may also be added to unoccluded topical dosage forms of the present invention if desired.

If the unoccluded topical dosage form of the present invention is an aerosol, foam or mouse, the composition will require a propellant for dispensing the composition from the container. The propellant may be any type of propellant commonly used in the cosmetic/pharmaceutical industry such as nitrogen, carbon dioxide, dimethyl ether, hydrocarbons, i.e., methane, ethane, propane, butanes and pentanes, halogenated hydrocarbons, i.e., $CH_2ClF$, $CClF_2CHClF$, $CF_3CHClF$, $CHF_2CClF_2$, $CHClFCHF_2$, $CF_3CH_2Cl$, $CClF_2CH_3$, $CHF_2CHF_2$, $CF_3CH_2F$ (HFC 134a), $CHF_2CH_3$ (HFC 152a), $CF_3CHFCF_3$ (HFC 227), $CF_3CF_3$ and $CF_3CF_2CF_3$. Some of the more commonly used hydrocarbon propellants are A-46 (15.2% propane/84.8% isobutene); and NP-46 (25.9% propane/74.1% n-butane), NIP-46 (21.9% propane/31.3% isobutene/46.8% n-butane). The amount of propellant will depend on the type of container for the composition of the present invention, the amount of the composition in the container, the amount of composition to be dispensed per actuation and the form in which the composition will be dispensed, i.e., mist or foam. The optimization of the propellant and container are within the ability of the skilled artisan and examples can be found in Wai-Chiu So et al., U.S. Pat. No. 6,946,120 and Remington, Science and Practice of Pharmacy, $21^{st}$ ed., pp. 1000-1017 which are incorporated in their entireties herein by reference. The propellant is generally not included in the calculation of the weight percentages of the composition prepared in accordance with the present invention because it is merely part of the dispensing device and typically does not remain part of the composition once the composition is dispensed and applied to the patient's skin.

The aerosols, foams and mousses of the present invention will include a solvent, preferably water and/or a lower alcohol, i.e., $C_1$-$C_6$ alcohols such as methanol, ethanol, isopropanol or mixtures thereof. The aerosols, foams or mousses may also comprise a co-solvent selected from one or more of the group consisting of aromatic and polyhydric alcohols such as 1,3-butylene glycol, propylene glycol, polyethylene glycol 400, hexylene glycol and dipropylene glycol or glycerol. When the co-solvent is present, it may be present in amounts of approximately 10% by weight or less, preferably approximately 5% by weight or less based upon the total weight of the composition.

The emulsions of the present invention are either water-in-oil (W/O) emulsions or oil-in-water (O/W) emulsions, and may include, but are not limited to, cetyl alcohol, glyceryl monostearate, lanolin, polyalkylsiloxanes, and stearic acid. Water-soluble ointment bases suitable for use in the present invention may be prepared from polyethylene glycols of varying molecular weight. Emulsion formulations are generally formed from a dispersed phase (e.g., a pharmacologically active agent), a dispersion medium and an emulsifying agent. If desired, emulsion stabilizers can be included in the formulation as well. Emulsifying agents suitable for use in such formulations include, but are not limited to, TWEEN 60®, Span 80®, cetostearyl alcohol, myristyl alcohol, glyceryl monostearate and sodium lauryl sulfate.

W/O emulsions may be prepared by taking a mixture of the active agent(s) with oil phase ingredients, bacteriostats/preservatives and buffer salts which are dissolved or suspended therein and to which water has been added to form a water-in-oil emulsion. O/W emulsions are semisolid emulsions, micro-emulsions, or foam emulsion systems containing the active agent(s). Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants.

Oral Compositions

One embodiment of the invention is directed to oral compositions for the administration of at least one cannabinoid, at least one terpene or the combination of at least one cannabinoid and at least one terpene. The oral compositions include both solid and liquid dosage forms. Solid dosage forms include but are not limited to tablets, capsules, pellets, granules, powders. The liquid dosage forms include syrups, solutions and suspensions. The oral compositions may be swallowed or applied to the oral cavity, i.e., sublingually, lingually or buccally. The oral compositions may be formulated to be immediate release, controlled release, or a combination thereof.

In embodiments of the present invention where the oral composition is a solid dosage form, the at least one cannabinoid, at least one terpene or the combination of at least one cannabinoid and at least one terpene may be combined with pharmaceutically acceptable excipients such as fillers, diluents, binders, stabilizing agents, lubricants, disintegrants or mixtures thereof. These pharmaceutically acceptable excipients are well known in the art and are described in Remington, the Science and Practice of Pharmacy, $21^{st}$ Ed. (2006), pp. 1058-1092, published by Lippincott Williams & Wilkins; United States Pharmacopeia 27 (2004), pp. 2809-2812; and Handbook of Pharmaceutical Excipients, $5^{th}$ Ed. (2006), published by the Pharmaceutical Press, both incorporated by reference. The solid oral dosage forms are made by methods commonly known in the art such as direct compression, wet or dry granulation, and extrusion spheronization. In one embodiment, the solid oral dosage form is a soft gel capsule wherein the at least one cannabinoid, at least one terpene or the combination of at least one cannabinoid and at least one terpene are dissolved or suspended in a suitable solvent, such as mineral or vegetable oil and mixed with other conventional excipients to prepare the soft gel capsule.

Examples of acceptable fillers, sometimes referred to as diluents, include water, sugars such as lactose, dextrose, sucrose, maltose, or microcrystalline cellulose, clays, and mixtures thereof.

Binders that are useful in the present invention include pharmaceutically acceptable substances with cohesive properties. Some examples include celluloses such as hydroxypropyl methylcellulose, hydroxypropyl cellulose and carboxymethycellulose sodium, polyvinylpyrrolidone, sugars, starches, and mixtures thereof.

Examples of stabilizing agents that are useful in the present invention include organic acids and alkaline metal salts of organic acids, such as succinic acid, fumaric acid, citric acid, sodium citrate, and mixtures thereof.

Examples of lubricants, glidants and/or antiadherents that may be used in the present invention include talc, magnesium stearate, calcium stearate, stearic acid, hydrogenated vegetable oils, polyethylene glycols, silicon dioxide, and mixtures thereof.

Examples of disintegrating agents that can be used in the present invention include corn starch, croscarmellose sodium, crospovidone (polyplasdone XL-10), sodium starch glycolate (EXPLOTAB® or PRIMOJEL®), or any combination of the foregoing.

The liquid dosage forms include syrups, solutions or suspensions. The syrups, solutions or suspensions of the present invention typically contain pharmaceutically acceptable excipients such as a liquid carrier, i.e., water and/or alcohol, solvent, flavoring agents, stabilizing agents, coloring agents, viscosity increasing agents or mixtures thereof. The pharmaceutically acceptable excipients employed in the syrups, solutions or suspensions of the present invention are described in Remington, the Science and Practice of Pharmacy, $21^{st}$ Ed. (2006), pp. 745-775, published by Lippincott Williams & Wilkins; United States Pharmacopeia 27 (2004), pp. 2809-2812; and Handbook of Pharmaceutical Excipients, $5^{th}$ Ed. (2006), published by the Pharmaceutical Press, incorporated by reference and further described below.

Examples of solvents have been previously described.

Flavoring agents that may be used in the present invention include peppermint, spearmint, wintergreen, cinnamon, coconut, coffee, chocolate, vanilla, menthol, licorice, anise, apricot, caramel, pineapple, strawberry, raspberry, grape, cherry, mixed berry, tropical fruits, mint, and mixtures thereof.

Coloring agents that may be employed in the present invention include FD&C-type dyes and lakes, fruit and vegetable extracts, titanium dioxide, and mixtures thereof.

Viscosity increasing agents have been described previously, and a few representative examples that may be included in the liquid dosage forms include methylcellulose, xanthan gum, carboxymethyl cellulose, hydroxypropyl cellulose, carbomer, acacia, agar, alginate, carrageenan, gum tragacanth, collagen, carboxypolymethylene, glyceryl monostearate, monostearate, polyvinylpyrrolidone, polyacrylamide, and mixtures thereof.

In certain embodiments, the composition of the present invention comprises a tablet, soft gelatin capsule or hard gelatin capsule for oral administration twice or three times a day wherein the tablet or capsule comprises a combination of THC and CBD along with a pharmaceutically acceptable carrier. Examples of methods for preparing the capsules and pharmaceutically acceptable excipients that may be used in the capsule can be found in U.S. Pat. Nos. 6,703,418 and 8,741,341, which are incorporated herein by reference. The THC may be in the form of dronabinol, also known as delta-9-tetrahydrocannabinol and Δ9-THC. The THC and CBD should be present in the tablet or capsule in a ratio of about 1:1 to about 1:200, preferably a ratio of about 1:2 to about 1:190 and most preferably a ratio of about 1:3 to about 1:180. In certain embodiments of the present invention, the amount of THC in the tablet or capsule will be equal to the amount of CBD or the amount of CBD will exceed the amount of THC. Some embodiments of the tablets and capsules will comprise THC and CBD in a weight ratio of THC to CBD ranging from a low value of 1:1; 1:2, 1:3, 1:4, 1:5, 1:6, 1:7, 1:8, 1:9 or 1:10 to an upper value of 1:200, 1:175; 1:150; 1:125; 1:100; 1:75: 1:50, 1:25, 1:20 or any values in between the lower and upper ranges. For examples the weight ratio of THC to CBD in the tablet or capsule may range for example from 1:2 to 1:150, 1:4 to 1:175, 1:5 to 1:100, 1:5 to 1:50 and any values between the upper and lower ranges including but not limited to the values provided in Example 1 herein.

In certain embodiments, the tablets or capsules are substantially free (i.e., less than 1 wt % of the total cannabinoid content, less than 0.5 wt % of the total cannabinoid content, less than 0.1 wt % of the total cannabinoid content) or free of any cannabinoid other than THC and CBD and are substantially free or free of any terpene.

Each tablet or capsule will further comprise: (i) about 1-100 mg of THC, preferably 2-75 mg of THC and most preferably 5-50 mg of THC and (ii) about 1-1000 mg of CBD, preferably 2-850 mg of CBD and most preferably 5-700 mg of CBD. The target of the oral administration of the tablet or capsule is to obtain a steady state plasma level of THC ranging from 0.25 ng/mL to 25 ng/mL, preferably 0.5 ng/mL to 17.5 ng/mL and most preferably 1 ng/mL to 12.5 ng/mL and a steady state plasma level of CBD greater than 0.5 ng/mL, preferably greater than 1 ng/mL and most preferably greater than 3 ng/mL. The oral administration of the tablet or capsule may begin at a lower dose and increased over 3 to 14 days until the desired dosing level is obtained with a twice or thrice a day administration that will provide the target steady state plasma level.

The foregoing tablet or capsule comprising the combination of THC and CBD is particularly useful in treating the symptoms of myotonic dystrophy type 1 (DM1) and type 2 (DM2) and improving the overall quality of the patient's life by reducing pain, anxiety and improving muscle movement of the all affected muscles, including gastrointestinal muscles. For example, the foregoing tablet or capsule comprising the combination of THC and CBD should reduce the time for muscle relaxation following contraction as measured by any conventional method employed in the art including but not limited to grip relaxation time as described in Logigian et al., "Mexiletine is an Effective Antimyotonia Treatment in Myotonic Dystrophy Type 1," *Neurology*, (2010) 74(18), pp. 1441-1448. More specifically, the reduction in time for muscle relaxation can be measured by determining the time required for relaxation of the grip or contraction of a patient's hand to relax following a three second maximal voluntary isometric contraction. A computer program measures the peak force during the three second contraction then measures the time to obtain various reductions in the peak force such as 90%, 75%, 50%, 25%, 5% and 0%. The reduction times are compared to a baseline obtained prior to treatment and after treatment, preferably 1-4 hours after initial administration, after 7 days of administration and/or after obtaining steady state plasma levels of THC and CBD. Similarly, administration of the foregoing tablet or capsule comprising the combination of THC and CBD should reduce the pain and/or anxiety a patient experiences as determined by use of a visual analog scale that measures pain intensity and a visual analog scale that measures anxiety. In addition, the administration of the foregoing tablet or capsule comprising the combination of THC and CBD should improve muscle weakness and/or delay the muscle deterioration as measured by any known analytical method such as the MFM-32 or MFM-20, or 6 minute walking test, previously described.

In certain embodiments, the composition of the present invention comprises a solution or suspension for oral administration twice or three times a day wherein the solution or suspension comprises a combination of THC and CBD along with a pharmaceutically acceptable liquid carrier. Examples of methods for preparing the solution or suspensions and pharmaceutically acceptable excipients that may be used in the solution or suspension can be found in U.S. Pat. Nos. 8,222,292 and 9,345,771, which are incorporated herein by reference. The THC and CBD should be present in the solution or suspension in a ratio of about 1:1 to about 1:200, preferably a ratio of about 1:2 to about 1:190 and most preferably a ratio of about 1:3 to about 1:180. In certain embodiments of the present invention, the amount of THC in the solution or suspension will be equal to the amount of CBD or the amount of CBD will exceed the amount of THC. Some embodiments of the solution or suspension comprising THC and CBD will contain a weight ratio of THC to CBD ranging from a low value of 1:1; 1:2, 1:3, 1:4, 1:5, 1:6, 1:7, 1:8, 1:9 or 1:10 to an upper value of 1:200, 1:175; 1:150; 1:125; 1:100; 1:75: 1:50, 1:25, 1:20 or any values in between the lower and upper ranges. For example, the weight ratio of THC to CBD in the tablet or capsule may range from 1:3 to 1:100, 1:4 to 1:75, 1:5 to 1:50, and any values between the upper and lower ranges including but not limited to the values provided in Example 2 herein.

In certain embodiments, the solutions or suspension are substantially free (i.e. less than 1 wt % of the total cannabinoid content, less than 0.5 wt % of the total cannabinoid content, less than 0.1 wt % of the total cannabinoid content) or free of any cannabinoid other than THC and CBD and are substantially free or free of any terpene.

Each dose of the solution or suspension will further comprise: (i) about 0.1-50 mg/mL of THC, preferably 0.5-25 mg/mL of THC and most preferably 1-20 mg/mL of THC and (ii) about 5-100 mg/mL of CBD, preferably 7.5-80 mg/mL of CBD and most preferably 10-50 mg/mL of CBD. The target of the oral administration of the solution or suspension is to obtain a steady state plasma level of THC ranging from 0.25 ng/mL to 25 ng/mL, preferably 0.5 ng/mL to 17.5 ng/mL and most preferably 1 ng/mL to 12.5 ng/mL and a steady state plasma level of CBD greater than 0.5 ng/mL, preferably greater than 1 ng/mL and most preferably greater than 3 ng/mL. The oral administration of the solution or suspension may begin at a lower dose and increased over 3 to 14 days until the desired dosing level is obtained with a twice or thrice a day administration that will provide the target steady state plasma level.

The foregoing solutions or suspensions comprising the combination of THC and CBD is particularly useful in treating the symptoms of myotonic dystrophy type 1 (DM1) and type 2 (DM2) and improving the overall quality of the patient's life by reducing pain, anxiety and improving muscle movement of eall affected muscles, including gastrointestinal muscles. More specifically, the foregoing solutions or suspensions comprising the combination of THC and CBD should reduce the time for muscle relaxation following contraction as measured by any conventional method employed in the art including but not limited to the previously described grip relaxation test. Similarly, administration of the foregoing solution or suspensions comprising the combination of THC and CBD should reduce the patient's pain and/or anxiety and should improve muscle weakness and/or delay the muscle deterioration as measured by any known analytical method such as previously described.

Nasal Compositions

One embodiment of the invention is directed to nasal compositions for the administration of the at least one cannabinoid, the at least one terpene, or the combination of at least one cannabinoid and at least one terpene. The nasal compositions may be in the form of a liquid, preferably a solution of suspension that can be sprayed onto or applied to the nasal passages via drops or swabs. In addition to the at least one cannabinoid, the at least one terpene, or the combination of at least one cannabinoid and at least one terpene, the nasal compositions may contain inert diluents and/or solvents commonly used in the art. Water is the preferred solvent, however, combinations of water with other physiologically acceptable solvents are also contemplated. Other solvents, solubilizing agents and emulsifiers suitable for use in place of, or in addition to, water include but are not limited to saturated aliphatic mono- and polyvalent alcohols which contain 2-6 carbon atoms (including, but not limited to, ethanol, 1,2-propylene glycol, sorbitol, and glycerine), polyglycols such as polyethylene glycols, and surfactants/emulsifiers like the fatty acid esters of sorbitan, and mixtures thereof. Oils, in particular, cottonseed, peanut, or corn oils, may also be added to the compositions. The combination of the additional solvents in the aqueous solution should preferably not exceed about 15% (w/v) of the total composition.

The nasal compositions of the present invention may further comprise one or more preservatives and/or one or more stabilizers. Preservatives that are suitable for use in the compositions of the invention include, but are not limited to, edetic acid and their alkali salts such as disodium EDTA and calcium EDTA, benzyl alcohol, methylparaben, propylparaben, butylparaben, chlorobutanol, phenylethyl alcohol, benzalkonium chloride, thimerosal, propylene glycol, sorbic acid, and benzoic acid derivatives. The preservatives should be used at a concentration of from about 0.001% to about 0.5% (w/v) in the final composition. The combination of benzalkonium chloride, used at a concentration of from about 0.001% to about 0.5%, preferably from about 0.005% to about 0.1% (w/v), and edetic acid (as a disodium salt), used at a concentration of from about 0.005% to about 0.1% (w/v), are the preferred preservative/stabilizer combination used in the liquid compositions of the present invention.

It is desirable that the nasal compositions of the present invention that are to be administered have a pH of about 4.5 to about 7.4, and preferably have a pH of about 5.5 to 7.1, for physiological reasons. Accordingly, in additional embodiments of the present invention, the compositions of the invention may further comprise one or more buffering agents that are used to adjust and/or maintain the compositions in the desired pH range. Examples of pH or buffering agents that are suitable for use in the compositions of the invention include, but are not limited to, citric acid, sodium citrate, sodium phosphate (dibasic, heptahydrate form), and boric acid or equivalent conventional buffers, and combinations thereof. The appropriate amounts of buffers and buffering agents, or combinations thereof, that are to be used in the compositions of the invention are described in the United States Pharmacopoeia, *Remington: The Science and Practice of Pharmacy*, and the like, the disclosures of which are incorporated herein by reference in their entireties.

The nasal compositions of the invention may also further comprise one or more taste-masking agents, one or more flavoring agents, one or more sweetening agents, and/or a combination of such agents.

In an embodiment of the invention, the nasal compositions may further comprise one or more water-soluble viscosity-increasing agents. Such agents are preferably used at the concentration of about 0.01% to about 5.0% (w/v), in order to typically produce a viscosity of the final solution between about 2 and about 300 centipoise. Viscosity-increasing agents that are suitable for use in accordance with the present invention include, but are not limited to, polyvinylpyrrolidones, cellulose derivatives including, but not limited to, hydroxyethyl cellulose, carboxymethyl cellulose or its salts, hypromellose, carrageenan, guar gum, alginates, carbomers, polyethylene glycols, polyvinyl alcohol, and xanthan gum.

Inhalation Compositions

One embodiment of the invention is directed to inhalation compositions for the administration of the at least one cannabinoid, the at least one terpene, or combination of at least one cannabinoid and at least one terpene to the respiratory system of the patient. The composition may be in the form of a powder, aerosol or vapor, which is inhaled by the patient to deliver the at least one cannabinoid, the at least one terpene or the combination of at least one cannabinoid and at least one terpene to the respiratory system of the patient, preferably the lungs.

The powders, solutions and suspensions that comprise the at least one cannabinoid, the at least one terpene, or combination of the at least one cannabinoid and the at least one terpene for delivery to the respiratory system of the patient may be prepared by any means commonly employed in the art, and employ excipients as described above for preparation of the solid and liquid oral dosage forms. The inhalation compositions may be delivered to a patient's respiratory system, using apparatuses commonly known in the art such as those described in U.S. Pat. Nos. 5,349,945; 5,394,868; 5,674,472; 5,766,573; 5,860,419; 6,641,800; 6,521,212; 9,339,507 and U.S. Patent Publication No. 2004/0265238 which are incorporated herein by reference.

Example 1

The following capsules comprising THC (dronabinol), CBD and sesame oil may be prepared as described in U.S. Pat. No. 6,703,418.

| CAPSULE A | | |
|---|---|---|
| | THC (mg) | CBD (mg) |
| 1 | 2.5 | 50 |
| 2 | 2.5 | 75 |
| 3 | 2.5 | 100 |
| 4 | 2.5 | 125 |
| 5 | 2.5 | 150 |
| 6 | 2.5 | 175 |
| 7 | 2.5 | 200 |
| 8 | 2.5 | 225 |
| 9 | 2.5 | 250 |
| 10 | 2.5 | 275 |
| 11 | 2.5 | 300 |
| 12 | 2.5 | 325 |
| 13 | 2.5 | 350 |
| 14 | 2.5 | 375 |
| 15 | 2.5 | 400 |
| 16 | 2.5 | 425 |
| 17 | 2.5 | 450 |

| CAPSULE B | | |
|---|---|---|
| | THC (mg) | CBD (mg) |
| 1 | 5 | 50 |
| 2 | 5 | 75 |
| 3 | 5 | 100 |
| 4 | 5 | 125 |
| 5 | 5 | 150 |
| 6 | 5 | 175 |
| 7 | 5 | 200 |
| 8 | 5 | 225 |
| 9 | 5 | 250 |
| 10 | 5 | 275 |
| 11 | 5 | 300 |
| 12 | 5 | 325 |
| 13 | 5 | 350 |
| 14 | 5 | 375 |
| 15 | 5 | 400 |
| 16 | 5 | 425 |
| 17 | 5 | 450 |

| CAPSULE C | | |
|---|---|---|
| | THC (mg) | CBD (mg) |
| 1 | 7.5 | 50 |
| 2 | 7.5 | 75 |
| 3 | 7.5 | 100 |
| 4 | 7.5 | 125 |
| 5 | 7.5 | 150 |
| 6 | 7.5 | 175 |
| 7 | 7.5 | 200 |
| 8 | 7.5 | 225 |
| 9 | 7.5 | 250 |
| 10 | 7.5 | 275 |
| 11 | 7.5 | 300 |
| 12 | 7.5 | 325 |
| 13 | 7.5 | 350 |
| 14 | 7.5 | 375 |
| 15 | 7.5 | 400 |
| 16 | 7.5 | 425 |
| 17 | 7.5 | 450 |

| CAPSULE D | | |
|---|---|---|
| | THC (mg) | CBD (mg) |
| 1 | 10 | 50 |
| 2 | 10 | 75 |
| 3 | 10 | 100 |
| 4 | 10 | 125 |
| 5 | 10 | 150 |
| 6 | 10 | 175 |
| 7 | 10 | 200 |
| 8 | 10 | 225 |
| 9 | 10 | 250 |
| 10 | 10 | 275 |
| 11 | 10 | 300 |
| 12 | 10 | 325 |
| 13 | 10 | 350 |
| 14 | 10 | 375 |
| 15 | 10 | 400 |
| 16 | 10 | 425 |
| 17 | 10 | 450 |

| CAPSULE E | | |
|---|---|---|
| | THC (mg) | CBD (mg) |
| 1 | 15 | 50 |
| 2 | 15 | 75 |
| 3 | 15 | 100 |
| 4 | 15 | 125 |
| 5 | 15 | 150 |
| 6 | 15 | 175 |
| 7 | 15 | 200 |
| 8 | 15 | 225 |
| 9 | 15 | 250 |
| 10 | 15 | 275 |
| 11 | 15 | 300 |
| 12 | 15 | 325 |
| 13 | 15 | 350 |
| 14 | 15 | 375 |
| 15 | 15 | 400 |
| 16 | 15 | 425 |
| 17 | 15 | 450 |

The capsule formulations A1-A17; B1-B17; C1-C17; D1-D17; E1-E17 may be administered to patients diagnosed with type 1 myotonic dystrophy so a target steady state plasma level of about 1 to 10 ng/mL of THC is obtained. Preferably, the capsules are administered once in the morning and once in the evening, i.e., every twelve hours, or if necessary, once in the morning followed by a second administration eight hours after the first morning administration and a third administration that occurs eight hours after the second administration.

One subset of patients will also be administered formulations A1-A17 twice a day for three days, B1-B17 twice a day for three days and C1-C17 twice a day for three days to determine if a dose escalation/titration will reduce adverse events associated with THC administration such as anxiety, nausea, dizziness and drowsiness.

The patients are asked to respond to a questionnaire regarding the perception of their pain prior to dosing, four hours after the initial dose, eight hours after the initial dose and 7-10 days after the initial dose, provided that the patient has complied with the twice or three times a day dosing for a 7-10 day period. The patient will also be asked to keep a daily diary that records their daily pain perception, as well as feelings of anxiety, nausea, dizziness and drowsiness.

A baseline time to 90%, 75%, 50%, 25%, 5% and/or 0% reduction in peak force pressure following a 3 second maximal voluntary isometric contraction of the left or right hand will be obtained for each patient prior to dosing. The baseline peak force will average three test trials, each test trial consisting of six (6) three second maximal voluntary contractions with a 10-20 second rest period between each of the six individual contraction/relaxation periods.

The patient's time to 90%, 75%, 50%, 25%, 5% and/or 0% reduction in peak force pressure will be obtained by the foregoing methodology 3-4 hours after initial dosing and 7-10 days after initial dosing.

There should be at least a 10%, 25%, 50% or more reduction from the baseline in the time for the patient to reach the 0-25% peak force contraction once the target steady state plasma level of about 1 to 10 ng/mL of THC is obtained.

The patients undergoing treatment may also be evaluated using the MFM-32 or MFM-20 scale, and 6 minute walking test prior to treatment, once a steady state plasma level of THC and CBD are obtained and at appropriate time points during the course of treatment such as one, two and three months during the course of treatment.

Example 2

The following solutions comprising THC (dronabinol), CBD and liquid carriers such as water, ethanol, polyethylene glycol, propylene glycol and combinations thereof may be prepared as described in U.S. Pat. No. 8,222,292:

| SOLUTION A | | |
|---|---|---|
| | THC (mg/mL) | CBD (mg/mL) |
| 1 | 0.5 | 10 |
| 2 | 0.5 | 15 |
| 3 | 0.5 | 20 |
| 4 | 0.5 | 25 |
| 5 | 0.5 | 30 |
| 6 | 0.5 | 35 |
| 7 | 0.5 | 40 |
| 8 | 0.5 | 45 |
| 9 | 0.5 | 50 |

| SOLUTION B | | |
|---|---|---|
| | THC (mg/mL) | CBD (mg/mL) |
| 1 | 0.75 | 10 |
| 2 | 0.75 | 15 |
| 3 | 0.75 | 20 |
| 4 | 0.75 | 25 |
| 5 | 0.75 | 30 |
| 6 | 0.75 | 35 |
| 7 | 0.75 | 40 |
| 8 | 0.75 | 45 |
| 9 | 0.75 | 50 |

| SOLUTION C | | |
|---|---|---|
| | THC (mg/mL) | CBD (mg/mL) |
| 1 | 1 | 10 |
| 2 | 1 | 15 |
| 3 | 1 | 20 |
| 4 | 1 | 25 |
| 5 | 1 | 30 |
| 6 | 1 | 35 |
| 7 | 1 | 40 |
| 8 | 1 | 45 |
| 9 | 1 | 50 |

| SOLUTION D | | |
|---|---|---|
| | THC (mg/mL) | CBD (mg/mL) |
| 1 | 1.5 | 10 |
| 2 | 1.5 | 15 |
| 3 | 1.5 | 20 |
| 4 | 1.5 | 25 |
| 5 | 1.5 | 30 |
| 6 | 1.5 | 35 |

SOLUTION D

| | THC (mg/mL) | CBD (mg/mL) |
|---|---|---|
| 7 | 1.5 | 40 |
| 8 | 1.5 | 45 |
| 9 | 1.5 | 50 |

SOLUTION E

| | THC (mg/mL) | CBD (mg/mL) |
|---|---|---|
| 1 | 2.0 | 10 |
| 2 | 2.0 | 15 |
| 3 | 2.0 | 20 |
| 4 | 2.0 | 25 |
| 5 | 2.0 | 30 |
| 6 | 2.0 | 35 |
| 7 | 2.0 | 40 |
| 8 | 2.0 | 45 |
| 9 | 2.0 | 50 |

SOLUTION F

| | THC (mg/mL) | CBD (mg/mL) |
|---|---|---|
| 1 | 2.5 | 10 |
| 2 | 2.5 | 15 |
| 3 | 2.5 | 20 |
| 4 | 2.5 | 25 |
| 5 | 2.5 | 30 |
| 6 | 2.5 | 35 |
| 7 | 2.5 | 40 |
| 8 | 2.5 | 45 |
| 9 | 2.5 | 50 |

SOLUTION G

| | THC (mg/mL) | CBD (mg/mL) |
|---|---|---|
| 1 | 3 | 10 |
| 2 | 3 | 15 |
| 3 | 3 | 20 |
| 4 | 3 | 25 |
| 5 | 3 | 30 |
| 6 | 3 | 35 |
| 7 | 3 | 40 |
| 8 | 3 | 45 |
| 9 | 3 | 50 |

The solution formulations A1-A9 to G1-G9 may be administered to patients diagnosed with type 1 myotonic dystrophy so a target steady state plasma level of about 1 to 10 ng/mL of THC is obtained. Preferably, 1 mL to 15 mL of one or a combination of more than one of the described solutions are administered once in the morning and once in the evening, i.e., every twelve hours, or if necessary, once in the morning followed by a second administration eight hours after the first morning administration and a third administration that occurs eight hours after the second administration.

One subset of patients will also be administered 1-15 mL of one or a combination of the above solutions twice a day for three days wherein each dose will comprise 2.5 mg of THC per dose for a total daily dose of 5 mg of THC and a total daily dose of 50 to 600 mg of CBD, 1-15 mL of one or a combination of the above solutions twice a day for three days wherein each dose will comprise 5 mg of THC for a total daily dose of 10 mg of THC and a total daily dose of 50 to 600 mg of CBD and 1-15 mL of one or a combination of the above solutions twice a day for three days wherein each dose will comprise 10 mg of THC for a total daily dose of 20 mg of THC and a total daily dose of 50 to 600 mg of CBD to determine if a dose escalation/titration will reduce adverse events associated with THC administration such as anxiety, nausea, dizziness and drowsiness.

The patients are asked to respond to a questionnaire regarding the perception of their pain prior to dosing, four hours after the initial dose, eight hours after the initial dose and 7-10 days after the initial dose, provided that the patient has complied with the twice or three times a day dosing for a 7-10 day period. The patient will also be asked to keep a daily diary that records their daily pain perception, as well as feelings of anxiety, nausea, dizziness and drowsiness.

A baseline time to 90%, 75%, 50%, 25%, 5% and/or 0% reduction in peak force pressure following a 3 second maximal voluntary isometric contraction of the left or right hand will be obtained for each patient prior to dosing. The baseline peak force will average three test trials, each test trial consisting of six (6) three second maximal voluntary contractions with a 10-20 second rest period between each of the six individual contraction/relaxation periods.

The patient's time to 90%, 75%, 50%, 25%, 5% and/or 0% reduction in peak force pressure will be obtained by the foregoing methodology, 3-4 hours after initial dosing and 7-10 days after initial dosing.

There should be at least a 10%, 25%, 50% or more reduction from the baseline in the time for the patient to reach the 0-25% peak force contraction once the target steady state plasma level of about 1 to 10 ng/mL of THC will be obtained.

The patients undergoing treatment may also be evaluated using the MFM-32 or MFM-20 scale prior to treatment, once a steady state plasma level of THC and CBD are obtained and at appropriate time points during the course of treatment such as one, two and three months during the course of treatment.

While certain preferred and alternative embodiments of the present invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

All documents, patents and other literature referred to herein are incorporated by reference in their entireties.

It is envisioned that any feature or element that is positively identified in this description may also be specifically excluded as a feature or element of an embodiment of the present invention as defined in the claims.

Example 3

The present example provide support for one embodiment of the present invention that a potential therapeutic effect of *Cannabis* for the treatment of myalgia and myotonia occurs through the presence of cannabinoid receptors in muscles and by modulation of both central and peripheral pain pathways.

Herein, the effects of a combination of THC/CBD is demonstrated in six patients with dystrophic and non-dystrophic myotonia in whom other therapies for myotonia/stiffness and myalgia failed to achieve any satisfactory response.

Patients and Methods

A combination of cannabidiol and tetrahydrocannabinol (CBD/THC) was prescribed as compassionate use to six consecutive patients complaining of myotonia and myalgia who were not satisfactorily responding to standard treatments. Genetically confirmed diagnoses were: myotonic dystrophy type 1 (2 patients), myotonic dystrophy type 2 (2 patients), and congenital myotonia due to mutations in CLCN1 (1 patient with Becker myotonia and 1 patient with Thomsen myotonia). Patients' age ranged from 25 to 65 years old, the male:female ratio was 1 (see Table 1).

tor treatment response: myotonia behaviour scale (MBS), hand opening time, fatigue severity scale (FSS, maximal score 63) and Epworth sleepiness scale (ESS, maximal score 24). Patients daily compiled diary visual analogue scales (length 10 cm) for myalgia and myotonia. The MBS is a patient-reported outcome validated in patients with non-dystrophic myotonia to assess the impact of myotonia in daily duties and activities. It consists of six statements and participants have to choose the one best describing their condition ranging from 0 (no stiffness) to 5 point (incapacitating stiffness). The hand opening time was assessed by video-documented timing hand opening with a stopwatch after tight hand closure for 5 seconds. Five consecutive trials were performed. Manual muscle testing was performed at baseline and at end of the $4^{th}$ week of treatment. MRC (Medical Research Council scale) was used to assess the

TABLE 1

Baseline clinical characteristic of 6 patients with myotonia.

|  | P1 | P2 | P3 | P4 | P5 | P6 |
| --- | --- | --- | --- | --- | --- | --- |
| Age, sex | 57, F | 65, F | 25, F | 54, M | 56, M | 25, M |
| Diagnosis | CLCN1 congenital myotonia | DM2 | DM1 | DM1 | DM2 | CLCN1- congenital myotonia |
| Symptoms at baseline | | | | | | |
| Grip myotonia | Yes | Yes | Yes | Yes | Yes | Yes |
| Leg stiffness | Yes | Yes | Yes | Yes | Yes | Yes |
| Myalgia | Yes, occasional | Yes, chronic | Yes, occasional | Yes, occasional | Yes, chronic | No |
| Muscle Weakness | No | Yes | No | Yes | Yes | No |
| GI symptoms | Yes | No | Yes | Yes | No | No |
| Assessments at baseline | | | | | | |
| MBS | 4 | 4 | 3 | 4 | 4 | 4 |
| Hand opening time (sec) | 10 | 12 | 3 | 5 | 5 | 5 |
| FSS | 54 | 46 | 30 | 53 | 49 | 9 |
| ESS | 10 | 6 | 8 | 19 | 5 | 4 |
| VAS-Pain | 7 | 3 | 1 | 0 | 5 | 0 |
| Therapy | | | | | | |
| Past medication for myotonia and myalgia | mexiletine lamotrigine flecainide phenytoine gabapentine | mexiletine methocarbamol carbamazepine pregabalin tolperisone | mexiletine lamotrigine carbamazepine flecainid | tolperisone carbamazepine methocarbamol | mexiletine tolperisone carbamazepine methocarbamol pregabalin | mexiletine lamotrigine tolperisone carbamazepine flecainid |
| Medication at baseline | none | none | none | none | none | none |

Abbreviations:
F = female;
M = male;
CLCN1 = Chloride channel N1;
DM1 = myotonic dystrophy type 1;
DM2 = myotonic dystrophy type 2;
GI = gastrointestinal tract;
MBS = myotonia behaviour scale;
FSS = fatigue severity scale;
ESS = Epworth sleeping scale;
VAS = visual analogue scale The compassionate use of CBD/THC oil was administered on a low dose (CBD:THC=10:1; 10.29 mg CBD twice a day and 1.10 mg THC twice a day) in the first 2 weeks and adjusted to a higher dose (CBD:THC=6:1; 20.58 mg CBD twice a day and 3.31 mg THC twice a day) in the following 2 weeks. The overall treatment lasted 4 weeks. During the compassionate use and in the follow-up period of 8 weeks, the following assessments were performed weekly to monistrength of neck flexors, shoulder abduction, elbow extension and flexion, wrist extension and flexion, hip flexion, knee extension and flexion, foot extension. In order to monitor the occurrence of side effects, each patient fulfilled a diary, listing the most common known side effects of medical *Cannabis* (constipation, bloating, sedation, depression/anxiety, dizziness/drowsiness, dry mouth, reflux, diarrhea, nausea/vomiting, weight gain). In addition, patients could add any other unusual complaints under the category "other" and they were interviewed about adverse events at evaluations.
Results:

The clinical features of patients at baseline are summarized in Table 1. All patients completed the 4 weeks of compassionate use. The most striking effect regarded the patients reported severity of myotonia as assessed by the myotonia behaviour scale (MBS). Almost all patients reported an improvement of myotonia in the last two weeks of compassionate use at the higher dose. MBS improved of at least 2 points in all patients. Overall the hand opening time improved in 5 out of 6 patients already in the first 2 weeks of treatment.

Both DM2 patients complained of chronic myalgia at therapy start, whereas the other patients mainly complained of occasional, mostly exercise-induced myalgia. CBD/THC therapy did not seem to significantly improve myalgia as no clear trend could be detected in the analysed Myalgia-VAS scales. Considering only patients affected by DM2 (Pt. 2 and 5) a significant improvement of myalgia was referred by Pt. 2; Pt. 5 instead experienced no relevant changes in the frequency or intensity of myalgia. Those patients complaining of gastrointestinal symptoms at baseline (abdominal pain, dysphagia, diarrhoea and irritable bowel syndrome) referred a significant improvement of abdominal pain and diarrhoea during treatment.

Side effects were mostly mild and did not cause any patient to withdraw therapy. The most common side effect was constipation, which was particularly evident at higher doses of CBD/THC. A detailed summary of patients' reported side effects is represented in Table 2.

TABLE 2

CBD/THC side effects in six myotonic patients

| Side effects | N of patients | Severity |
| --- | --- | --- |
| Constipation | 4/6 | moderate |
| Bloating | 2/6 | mild |
| Sedation | 1/6 | mild |
| Depression/Anxiety | 1/6 | mild |
| Dizziness/drowsiness | 0/6 | — |
| Dry mouth | 0/6 | — |
| Reflux | 0/6 | — |
| Diarrhoea | 0/6 | — |
| Nausea/vomiting | 0/6 | — |
| Weight gain | 0/6 | — |
| Other | 0/6 | — |

The monitoring of fatigue and daytime sleepiness with the FSS and ESS did not show any relevant increase of fatigue or daytime sleepiness in the treated patients.
Major clinical improvements were observed in particular in patients 2 and 6. A detailed description of their disease history and response to CBD/THC treatment is provided hereafter.
Case Report: Patient 2

This 65 years-old woman was diagnosed with DM2 at the age of 54 years. As DM2-related comorbidities she has diabetes mellitus type 2 without diabetic neuropathy, and controlled paroxysmal atrial fibrillation. Her main muscular complaints have always been a severe grip myotonia and myotonia of the legs while walking, as well as persistent myalgia especially at lower back. In the last several years she developed a proximal and axial muscle weakness (MRC grade 4). Several drugs have been tried in the past to improve her myotonia e.g. mexiletine, carbamazepine, pregabalin and were suspended due to inefficacy and risk of cardiac arrhythmias. Her myalgia was unsuccessfully treated with methocarbamol, ibuprofen, and pregabalin. After discussing potential risks and benefits, a compassionate use with low dose CBD/THC has been started. In the first 2 weeks of the treatment this patient reported a relevant improvement of myotonia at both hands and legs. This improvement was confirmed on the MBS scale by improvement from 4 to 1, and on the hand opening time declined from 12 sec. to 3 sec. Even more promising, after 2 weeks she could climb up stairs more rapidly and with less muscle stiffness and even repetitive squatting could be performed now for the first time in 4 years. These improvements are probably due to the significant improvement of proximal muscle myotonia and myalgia. She complained of no relevant side effects and no increase of FSS and ESS scores was observed. A doubling of the CBD dose after week 4 of treatment for another 8 weeks did not lead to any greater improvements.

Case Report: Patient 6

This 25 years-old male was diagnosed with CLCN1-congenital myotonia at the age of 10 years. He has a severe therapy-resistant grip and generalized myotonia. Previous treatments with mexiletine improved the myotonia but he developed, as drug-related side effect, a severe major depression that completely resolved on drug discontinuation as alternatives to mexiletine, lamotrigine, tolperisone, carbamazepine, and flecainid have been administered over time. However, no relevant improvement of myotonia was obtained. He then received as compassionate use CBD/THC and experienced a marked improvement of myotonia in the last 2 weeks of treatment (higher CBD/THC dose). For this patient the lower dose (10:1) was not effective at all due to the high BMI of this patient (200 cm height, weight 117 Kg) who then responded on the higher dose. He reported no relevant side effects.

Discussion:

In this example, the effect of cannabinoids prescribed as compassionate use to six patients with dystrophic and non-dystrophic myotonias were prescribed for the first time. The term cannabinoids refer to any drug able to act on the endocannabinoid system, which is widely expressed in the central and peripheral nervous system. Cannabinoids mainly exert their effects by binding to two G-coupled protein receptors (GCPRs): CB1 and CB2; however other receptors (GPR55, GPR119, TRPV1, etc.) are also known to be involved. CB1 are expressed in nearly all tissues but especially in the presynaptic neurons of CNS, dorsal root ganglia and spinal cord. CB2 receptors are mainly present on immune cells and in small amounts also in the CNS. The plant Cannabis sativa contains more than 100 different cannabinoids and among those the best studied and used for their medical properties are cannabidiol (CBD) and tetrahydrocannabinol (THC). THC binds and activates CB1 and CB2; it exerts, besides well-known psychoactive effects, many other regulatory functions on appetite, pain modulation, neuroprotection, cognitive functions and coordination mostly mediated by CB1 receptors as well as anti-inflammatory and immunological effects mediated by CB2. CBD has a lower binding affinity for CB receptors; it is usually safe, well tolerated and able to counteract the psychoactive effects of THC antagonizing CB1 receptors by allosteric or indirect mechanisms. CBD also exerts an anti-inflammatory and analgesic effect as an inverse agonist of CB2 receptors and a TRPV1 agonist. The balance of THC and CBD is then responsible for the safety and therapeutic effect of Cannabis based products. Different ratios and formulations of CBD and THC (oil, oromucosal spray, capsules, oral solutions) have proven empirical efficacy in different conditions (spasticity in multiple sclerosis, treatment resistant epilepsies, nausea and vomiting due to chemotherapy, chronic pain, reduced appetite and weight loss associated with HIV/AIDS, and many other diseases as off label therapy). The rationale for prescribing CBD/THC to patients with dystrophic and non-dystrophic myotonia lies on anecdotal reports of efficacy partly supported by the recent evidences regarding the presence of cannabinoid receptors in human skeletal muscle. Great heterogeneity is found in the literature as regards types of *Cannabis* based products, pharmacokinetics, CBD/THC composition, so that establishing the optimal dosing strategy is difficult. Nabiximols is a cannabinoid drug licenced also in Germany for the treatment of multiple sclerosis with a 1:1 ratio of CBD/THC. To ensure peripheral CBD/THC effects by minimizing central nervous system side effects of cannabinoids, a nabiximols composition was adopted for patients to a lower concentration of THC, to a 10:1 (low ratio dose) and 6:1 (high ratio dose) ratios of CBD/THC. All six treated patients experienced various degrees of improvement of myotonia, especially if assessed by the myotonia behaviour scale. These changes in MBS correlated with higher doses of CBD/THC. Objective improvements of myotonia were also detected by measuring the hand opening time, already in the first 2 weeks of treatment, thus mostly anticipating changes in MBS. The higher ratio of CBD/THC did not produce further improvements of hand-opening time. Muscle relaxation and reduced spasticity are well-documented effects of *Cannabis*-based products; it is however believed that these effects are mainly due to central nervous mechanisms. Novel insights on the peripheral effects of cannabinoids in skeletal muscles are provided by Olah et al. and might partially explain the reduction of myotonia, muscle stiffness and myalgias observed in our patients. In this study in vitro and in vivo (CB1 knockout animal model) were used to show that cannabinoid interfere with intramuscular $Ca^{2+}$ homeostasis and excitation-contraction coupling (ECC). Muscular CB1 receptors are localized on the I-bands around the Z-lines of adult muscle fibres and their activation through a selective agonist inhibited the ryanodine receptor-mediated sarcoplasmic release of $Ca^{2+}$ and reduced the $Ca^{2+}$ sensitivity of contractile proteins thus reducing muscle contraction. Besides CB1, also CB2 and TRPV1 receptors are known to be expressed in human skeletal muscle, however most of their functions is largely unknown. Preliminary data have shown an involvement in regulating muscular glucose uptake, energy metabolism and formation of muscle fibres. The injection of CBD in dystrophic mdx mice promoted myotube formation and reduced inflammation mostly via activation of TRPV1 and TRPA1. The potential implication of these aspects in myotonia and myalgia still needs to be investigated.

Recent metanalyses showed moderate evidence of efficacy of *Cannabis*-based medicinal products for pain relief and opioid-sparing effect in many different forms of chronic pain as cancer pain, neuropathic pain and fibromyalgia. Both DM2 patients complained of persistent myalgia, and, in order to determine potential improvements of pain while on CBD/THC, patients daily compiled pain-VAS. One patient presented a clear improvement of myalgia (Case 2). A subset of myalgia patients may benefit from cannabinoids, as it has been observed in clinical trials in multiple sclerosis where patients have been classified as responders or non-responders. The origin and pathophysiology of myalgia in DM2 patients is still largely unclear. Moshurab et al. examined 35 DM2 patients with quantitative sensory testing (QST) and transcriptome analysis on muscle biopsies. They found that DM2 patients had altered pain pressure thresholds, mechanical pain sensation and wind-up ratios in comparison to controls, thus suggesting the presence of peripheral sensitization mechanisms known to be a trigger for central sensitization. The endocannabinoid system plays a central role in the inhibition of nociceptive transmission acting at supraspinal (thalamus, limbic system, periaqueductal gray) spinal and peripheral levels. This peripheral nociceptive modulation is believed to be mainly due to CB2, TRPV1 receptors and other indirect mechanisms also involving the opioid system. Cannabidiol as used in patients is known to have a CB2- and TRPV1-mediated anti-inflammatory and analgesic function and to upregulate µ- and δ-opioid receptors with a mechanism mediated by serotonin receptor (5-HT1A). The only assessment method for myalgia has been pain-VAS making it difficult to assess whether the improvement experienced is mainly due to peripheral or central mechanisms. Furthermore, by improvement in both, myalgia and myotonia, the DM2 patient gained strength and was again able to perform repetitive squats for the first time in 4 years.

Overall, the compassionate use of CBD/THC was well tolerated in all patients, the most consistent complaint was constipation experienced in four of six patients. Central side effects as sedation, depression, increased fatigue were not frequent, probably due to the reduced CBD:THC ratio. Some patients reported an improvement of some gastrointestinal symptoms (abdominal pain, diarrhoea), known to occur often in the myotonic dystrophy population. The effects of cannabinoids on the gastrointestinal system are also increasingly studied in the last years. CB1 and CB2 are highly expressed throughout the intestinal mucosa and enteric nerves; they act mostly regulating/reducing the accelerated GI motility, so that in particular patients with irritable bowel syndrome seem to benefit from *Cannabis*-based products.

These results show promising effects of cannabinoids for the symptomatic treatment of myotonia and myalgia. Given the low prevalence of central side effects in patients, low to mid CBD:THC ratio of 6:1 to 3:1 might be considered in future trials and on an individual patient basis.

The invention described herein may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the claims.

The invention claimed is:
1. A method for treating the symptoms of myotonia in a subject having dystrophic or non-dystrophic myotonia comprising orally administering a therapeutically effective amount of cannabidiol (CBD) and tetrahydrocannabinol (THC) to the subject in a formulation, wherein the formu- lation contains a weight ratio of CBD to THC of about 1:1 to about 10:1, respectively, in pharmaceutically-acceptable excipients.

2. The method of claim 1 where the myotonia is dystrophic myotonia.

3. The method of claim 1 where the mytonia is non-dystrophic myotonia.

4. The method of claim 2 where the subject has myotonic dystrophy type 1 (DM1).

5. The method of claim 2 where the subject has myotonic dystrophy type 2 (DM2).

6. The method of claim 4 where the symptoms of DM1 are disabling grip.

7. The method of claim 5 where the symptoms of DM2 are painful stiffness in the subject's legs and neck.

8. The method of claim 1 wherein the formulation contains CBD/THC in an oil.

9. The method of claim 1 wherein the formulation is administered twice a day.

10. The method of claim 1 wherein the CBD to THC is in a ratio of about 1:1 to about 6:1, respectively, administered twice a day.

11. The method of claim 1 wherein CBD to THC is in a ratio at a range of about 6:1 to about 3:1.

12. The method of claim 10 where the subject has CLCN1-congential myotonia.

13. A method for treating the symptoms of myotonia in a therapy-resistant subject having dystrophic or non-dystrophic myotonia comprising orally administering a therapeutically effective amount of cannabidiol (CBD) and tetrahydrocannabinol (THC) to the subject in a formulation, wherein the formulation contains a weight ratio of CBD to THC of about 1:1 to about 10:1, respectively, in pharmaceutically-acceptable excipients.

14. The method of claim 13 where the subject is resistant to therapies selected from a group consisting of mexiletine treatment, lamotrigine treatment, tolperisone treatment, carbamazepine treatment, pregabalin treatment, flecainid treatment, and combinations thereof.

15. The method of claim 13 where the subject has CLCN1-congential myotonia.

16. The method of claim 13 wherein the CBD to THC is in a ratio of 6 to 1, respectively, administered twice a day.

17. The method of claim 1 wherein the oral administration is sublingually, lingually or buccally.

* * * * *